US009380803B2

(12) United States Patent
Sworn et al.

(10) Patent No.: US 9,380,803 B2
(45) Date of Patent: Jul. 5, 2016

(54) XANTHAN GUM

(75) Inventors: Graham Sworn, Montlignon (FR);
Emmanuel Kerdavid, Vincennes (FR);
Paule Chevallereau, Melle (FR); José Fayos, Paris (FR)

(73) Assignee: DUPONT NUTRITION BIOSCIENCES APS (DK)

( * ) Notice: Subject to any disclaimer, the term of this patent is extended or adjusted under 35 U.S.C. 154(b) by 94 days.

(21) Appl. No.: 13/260,876

(22) PCT Filed: Mar. 30, 2010

(86) PCT No.: PCT/EP2010/054183
§ 371 (c)(1),
(2), (4) Date: Sep. 28, 2011

(87) PCT Pub. No.: WO2010/112499
PCT Pub. Date: Oct. 7, 2010

(65) Prior Publication Data
US 2012/0021112 A1    Jan. 26, 2012

(30) Foreign Application Priority Data
Apr. 2, 2009   (EP) .................. 091572172

(51) Int. Cl.
| A21D 10/00 | (2006.01) |
| A23L 1/054 | (2006.01) |
| C08B 37/00 | (2006.01) |
| C08L 5/00 | (2006.01) |
| C12P 19/06 | (2006.01) |

(52) U.S. Cl.
CPC .......... *A23L 1/0541* (2013.01); *C08B 37/0033* (2013.01); *C08L 5/00* (2013.01); *C12P 19/06* (2013.01)

(58) Field of Classification Search
USPC ........................................ 426/549
See application file for complete search history.

(56) References Cited

U.S. PATENT DOCUMENTS

| 4,978,750 A | 12/1990 | Wilke et al. |
| 6,083,890 A * | 7/2000 | Miskiel et al. ............... 510/108 |
| 6,316,614 B1 | 11/2001 | Doherty et al. |

FOREIGN PATENT DOCUMENTS

| DE | 3783145 | 6/1993 |
| EP | 0233019 | 8/1987 |
| EP | 0765939 | 4/1997 |

OTHER PUBLICATIONS

English translation of WO 1997018263.*
Bradshaw, I.J., et al., Carbohydr. Polym., 3, (1983) pp. 23-38.
Cheetham, N.W.H., et al., Carbohydr. Polym., 10 (1989) pp. 55-60.
(Continued)

*Primary Examiner* — Michele L Jacobson
*Assistant Examiner* — Katherine D Leblanc

(57) ABSTRACT

Xanthan gums with improved characteristics are provided, a method for preparing the xanthan gums as well as compositions and products comprising the xanthan gums. In particular, the invention relates to xanthan gums obtained from *Xanthomonas campestris* strains, pathovar *cynarae* CFBP 19, *juglandis* CFBP 176, *pelargonii* CFBP 64, *phaseoli* CFBP 412 or ATCC 17915, *celebenois* ATCC 19046, or *corylina* CFBP 1847 or from a derivative or progeny thereof and to methods of producing xanthan gum from these strains.

12 Claims, 13 Drawing Sheets

(56) References Cited

OTHER PUBLICATIONS

Christensen, et al., Carbohydrates and Carbohydrate Polymers. Analysis, Biotechnology, Modification, Antiviral, Biomedical and Other Applications, M. Yalpini (ed.) ATL Press (1993) pp. 166-173.
Flores Candia, J.-L., et al., Biotechnol. Prog., 15 (1999), pp. 446-452.
Hassler, R.A. et al., Biotechnol. Prog., 6, (1990) pp. 182-187.
Morris, et al., J. Mol. Biol., 110 (1977) pp. 1-16.
Paradossi, G., et al., Biomacromolecules, ACS, Washington, DC, US, vol. 3, No. 3, pp. 498-504; XP002568691A, Jan. 1, 2002.
Peters, H.-U. et al., Biotechnology Letters, vol. 15 (1993), pp. 565-566.
Sanchez, A., et al., World Journal of Microbiology and Biotechnology, vol. 13, No. 4, pp. 443-451, XP002589167A, Jul. 4, 1997.
Schorsch, C., et al., Carbohydrate Polymers, Elsevier Science, Ltd. vol. 34, No. 3, pp. 165-175; XP004101334A, Dec. 20, 1997.
Shatwell, K. P., et al., Carbohydr. Polym., 14, (1991) pp. 29-51.
Shatwell, K.P. et al., Carbohydr. Polym., 14, (1991) pp. 115-130.
Shatwell, K.P., et al., Carbohydr. Polym., 14, (1991) pp. 131-147.
Wang, F., et al., J. of Food Science, vol. 67, (2002) pp. 2609-2614.
Smith, I.H. et al., "Influence of pyruvate content of xanthan on macromolecular association in solution," *Int. J. Biol. Macromol.*, 1981, vol. 3, April.
Shatwell, K. et al., "Influence of the Acetyl Substituent on the Interaction of Xanthan with Plant Polysaccharides—III. Xanthan-Konjac Mannan Systems," *Carbohydrate Polymers*, vol. 14, 1991, pp. 131-147.
Morrison, N. et al. "New Forms of Xanthan Gum with Enhanced Properties." The Royal Society of Chemistry 2004., pp. 124-130.

\* cited by examiner

XANTHAN GUM

CLAIM FOR PRIORITY

This application claims priority under 35 USC 371 to International Application No. PCT/EP2010/054183, filed on Mar. 30, 2010, which claims priority to European Application No. 09157217.2, filed on Apr. 2, 2009, each of which is hereby incorporated by reference in its entirety.

FIELD OF THE INVENTION

The present invention relates to novel xanthan gums with improved characteristics, a method for preparing the xanthan gums as well as compositions and products comprising the xanthan gums. In particular, the invention relates to xanthan gums obtained from *Xanthomonas campestris* strains, *pathovar cynarae* CFBP 19, *juglandis* CFBP 176, *pelargonii* CFBP 64, *phaseoli* CFBP 412 or ATCC 17915, *celebenois* ATCC 19046, or *corylina* CFBP 1847 or from a derivative or progeny thereof and to methods of producing xanthan gum from these strains.

BACKGROUND OF THE INVENTION

Figure 2:
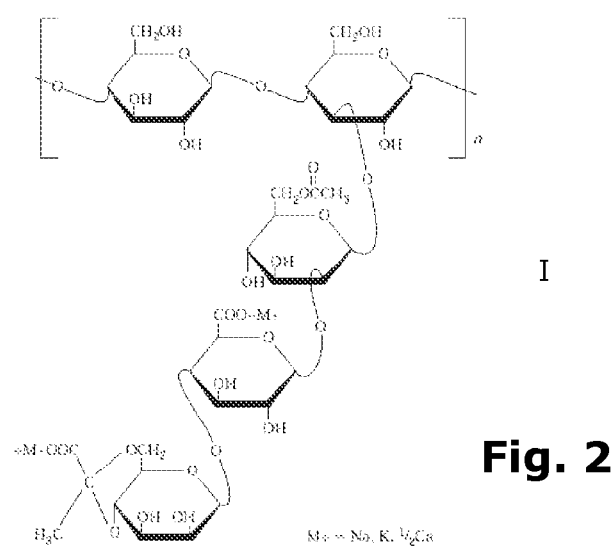

The polysaccharide xanthan gum is produced by the microorganism *Xanthomonas campestris* and has the primary structure shown in Formula I, which is shown in FIG. 2.

Xanthan gum consists of a cellulosic backbone of β-1,4 linked D glucose units substituted on alternate glucose residues with a trisaccharide side chain. The trisaccharide side chain is composed of two mannose units separated by a glucuronic acid. Approximately half the terminal mannose units are linked to a pyruvate group and the non-terminal residue usually carries an acetyl group. The carboxyl groups on the side chains render the gum molecules anionic. Xanthan gum has a molecular weight of about $2\times10^6$ Daltons with a narrow molecular weight distribution compared to most polysaccharides. X-ray diffraction studies on xanthan gum fibres have identified a right handed, five fold helix conformation. In this conformation the side chains are aligned with the backbone and stabilise the overall conformation. In solution the side chains wrap around the cellulose-like backbone thereby protecting it. It is believed that this is responsible for the excellent stability of xanthan gum under adverse conditions.

Two of the key functionalities of xanthan gum that set it apart from other hydrocolloid thickeners are its rheology and its ability to interact synergistically with galactomannans.

The rheology can be characterised by the development of very high viscosity at low shear rates and pseudoplastic flow which provide suspension stability to finished products and low viscosity at higher shear rates for ease of filling, pouring and pumping.

Xanthan gum also has the ability to interact with galactomannans such as guar gum, cassia gum, tara gum and locust bean gum and with structurally similar polysaccharides such as the glucomannan konjac. This interaction results in either a synergistic increase in viscosity in the case of guar gum or the formation of strong self supporting gels as seen with locust bean gum and konjac glucomannan.

These functionalities are used in a wide range of food applications and maximising these through control of the xanthan structure and manufacturing process would provide a high performance xanthan gum of real benefit to the customer, in terms of cost in use.

Synergy

Initial studies (Morris, E. R., Rees, D. A., Young, G., Walkinshaw, M. D. and Darke, A. "Order-Disorder transition for a bacterial polysaccharide in solution. A role for polysaccharide conformation in recognition between *Xanthomonas* pathogen and its plant host." *J. Mol. Biol.*, 110 (1977) 1-16.) proposed a model in which the unsubstituted, galactose free (smooth) regions of the galactomannans (glucose free in the case of konjac mannan) bind to xanthan in its ordered state. This model has been used to explain the difference in degree of interaction between galactomannans of differing degrees of substitution. Subsequent studies, which showed that interactions were enhanced after heating the mixture to temperatures above the coil-helix transition of the xanthan, were interpreted as evidence that the binding occurred with the cellulosic backbone of the xanthan gum in the ordered state. An alternative explanation was that when the hydrocolloids are mixed at temperatures below the setting point of the gel, they form an inferior, disrupted network with melting and resetting giving a stronger, coherent gel.

The degree/strength of associations is increased as galactose substitution is decreased. For example locust bean gum which has a galactose content of 17-26% forms self supporting gels with xanthan gum whereas guar gum which has a galactose content of 33-40% forms weak gel networks resulting in a synergistic increase in viscosity. The molecular weight of the galactomannans is also known to influence their interactions with xanthan gum. The lower the molecular weight, the weaker the interactions seen with xanthan gum. It has been reported that increasing the ionic strength of the solvent reduces the associations between xanthan and galactomannans/glucomannans: for example increasing salt concentrations or lowering of pH results in weaker gels or lower viscosity in the mixtures.

Xanthan Molecular Structure and its Influence on Functionality

The role of the acetate and pyruvate groups in the molecular structure of xanthan gum and their impact on functionality is probably the most widely studied aspect of the structure-function relationship. Particular emphasis has been given to their role in controlling the rheology of the xanthan gum and their influence on interactions with the galactomannans. Assuming only one acyl group per side chain, the stoechiometric amounts of acetyl and pyruvate are 5.0% and 8.1% respectively. Xanthan gum sold commercially contains between 3 and 4% acetate and between 4 and 5% pyruvate. The strength of gels of xanthan and locust bean gum or konjac mannan have been shown to be very dependent on the degree of acetyl substitution (Wang, F., Wang Y.-J. and Sun, "Z. Conformational role of xanthan in its interaction with locust bean gum." *J. Food Science*, 67 (2002) 2609-2614; Shatwell, K. P., Sutherland, I. W., Ross-Murphy, S. B. and Dea, I. C. M. "Influence of the acetyl substituent on the interaction of xanthan with plant polysaccharides—I. Xanthan—locust bean gum systems." *Carbohydr. Polym.*, 14 (1991) 29-51; Shatwell, K. P., Sutherland, I. W., Ross-Murphy, S. B. and Dea, I. C. M. "Influence of the acetyl substituent on the interaction of xanthan with plant polysaccharides—III. Xanthan—konjac mannan systems." *Carbohydr. Polym.*, 14 (1991) 131-147). Shatwell et al concluded that the interactions increase with decreasing acetylation. This resulted in stronger gels with LBG and konjac mannan, a result also seen by others. They also suggested that low-acetate xanthan had stronger interactions with guar gum compared to standard xanthan, something which has also been reported in several other studies. Morrison et al. showed evidence for this in the form of increased viscosity at 1 s$^{-1}$ in low-acetate xanthan/guar mixtures compared to standard xanthan/guar mixtures.

There is very little evidence to suggest that the pyruvate content of xanthan has an influence on interactions with galactomannans. Shatwell et al indicated that gel strength with LBG reduced slightly with reduction of pyruvate level but results were not conclusive since the molecular weight of the low-pyruvate samples was lower than standard xanthan.

It has been shown by several workers that the pyruvate content of xanthan has a strong influence on the viscosity of the product. The viscosity increases with increasing pyruvate content. Flores and Deckwer suggested that there is not a continuous relationship between pyruvate content and viscosity, but rather, that there is a step increase when going from below 2% to above 3% pyruvate (Flores Candia, J.-L. and Deckwer, W.-H. "Effect of the nitrogen source on pyruvate content and rheological properties of xanthan." *Biotechnol. Prog.*, 15 (1999) 446-452).

It has also been demonstrated that the viscosity of low pyruvate xanthan is less sensitive to the addition of salts (Cheetham, N. W. H. and Norma, N. M. N. "The effect of pyruvate on viscosity properties of xanthan." Carbohydr. Polym., 10 (1989) 55-60).

There is one published paper that contradicts this and claims that pyruvate content has no significant effect on solution viscosity and they attributed the differences observed by other workers to possible differences in molecular weight (Bradshaw, I. J. Nisbet, B. A., Kerr, M. H. and Sutherland, I. W. "Modified xanthan—its preparation and viscosity." *Carbohydr. Polym.*, 3 (1983) 23-38). However, in this study, viscosity was measured at shear rates between 8.8 and 88.8 s$^{-1}$. These relatively high shear rates may account for the lack of difference in measured viscosity. Generally the viscosity differences are far more marked at shear rates below 0.1 s$^{-1}$. Christensen et al (Christensen, B. E., Smidsrod, O and Stoke, O. "Xanthans with partially hydrolysed side chains: Conformation and transitions." In *Carbohydrates and Carbohydrate Polymers. Analysis, Biomedical and other Applications*. M. Yalpini (ed.), ATL press (1993) pp 166-173) have shown that the terminal β-mannose is relatively susceptible to acid hydrolysis so low pyruvate samples prepared in this way may also have reduced molecular weight due to removal of this sugar. Since acid hydrolysis has been used to prepare low pyruvate xanthan samples in many of the referenced studies, further work is needed to separate the effects of molecular weight from the effects of pyruvate content.

The presence of acetate on the other hand tends to reduce xanthan gum viscosity (Hassler, R. A. and Doherty, D. H. "Genetic engineering of polysaccharide structure: Production of variants of xanthan gum in *Xanthomonas campestris*". *Biotechnol. Prog.*, 6 (1990) 182-187). It has been shown that an acetate-free xanthan has higher viscosity than native xanthan. Some work has been done on trying to identify distribution of acetate and pyruvate by fractional precipitation with ethanol to differentiate xanthan preparations into fragments with differing pyruvate content (Shatwell, K. P., Sutherland, I. W., Ross-Murphy, S. B. and Dea, I. C. M. "Influence of the acetyl substituent on the interaction of xanthan with plant polysaccharides—III. Xanthan—konjac mannan systems." *Carbohydr. Polym.*, 14 (1991) 131-147). It was found that as the alcohol level increased the pyruvate level in the precipitated fraction increased. This has also been achieved using an affinity matrix prepared by coupling antibodies to a *Rizobium* polysaccharide to a Sepharose gel column (Shatwell, K. P., Sutherland, I. W., Ross-Murphy, S. B. and Dea, I. C. M. "Influence of the acetyl substituent on the interaction of xanthan with plant polysaccharides—II. Xanthan—guar gum systems." *Carbohydr. Polym.*, 14 (1991) 115-130). Using this technique it was possible to identify a pyruvate-rich and pyruvate-poor fraction from the same xanthan preparation indicating some heterogeneity in the distribution of pyruvate. The implications of this for functionality were not discussed.

Methods to Control Xanthan Molecular Structure

A considerable amount of work has also been done on methods of controlling the levels of acetate and pyruvate during production of xanthan gum and Tables 1 and 2 summarise the techniques for the control of these substituent groups. These include the selection or modification of the *Xanthomonas* strain, control of certain parameters during the fermentation or post fermentation treatment during recovery of the gum.

TABLE 1

A summary of the known techniques available for the control of the acetate level in xanthan

| Method of control | Advantages | Disadvantages |
| --- | --- | --- |
| Post fermentation treatment Heat treatment at alkaline pH Enzymatic methods | Has been successfully performed at pilot scale | Variable acetate content Reduction in Mw Specific enzymes not described |
| Genetic control of strain (KELTROL/KELZAN ASX) | OK for 0% acetate Preservation of Mw | Not suitable for intermediate acetate levels GMO issue |

TABLE 2

A summary of the known techniques available for the control of the pyruvate level in xanthan.

| Method of control | Advantages | Disadvantages |
| --- | --- | --- |
| Fermentation conditions Nitrogen content during fermentation Oxygen availability | Consistent pyruvate content (high or low) Low viscosity broth Preservation of Mw | Yield? |
| Post fermentation treatment Heat treatment at acid pH Enzymatic methods | No GMO issues | Variable pyruvate content Reduction in Mw (loss of terminal β-mannose?) Specific enzymes not described |
| Genetic control of strain | OK for 0% pyruvate Low viscosity broth Preservation of Mw | Not suitable for intermediate pyruvate levels GMO issue |

Strains of *Xanthomonas campestris*

Hassler and Doherty (cf. above) evaluated the properties of xanthan prepared from *Xanthomonas campestris* mutants obtained by genetic engineering. These strains carried a chromosomal deletion mutation that eliminated the entire gum gene cluster in their genome. The gum gene cluster was instead present in each strain on a recombinant plasmid. The gum gene mutations were present in these cloned gum genes. These mutants were defective in the xanthan biosynthetic pathway and produced xanthan that varied in the content and position of the acetate and pyruvate groups. The 6 possible variations are summarised in FIG. 1. They found that, when pyruvylation of the outer mannose is blocked by mutations that inactivate ketalase, high-level acetylation of the outer mannose results (variant 4). They concluded that variant 3 (high-pyruvate, low-acetate) gave the highest viscosity and that the presence of acetate decreased viscosity regardless of its position.

Viscosity measurements were made on xanthan recovered from broths that were not subjected to a thermal treatment.

Therefore the viscosity values reflect those of the native polymer. No studies were made on other aspects of functionality such as salt tolerance, acid stability, hydration or interaction with galactomannans.

European patent application EP 0 765 939 discloses zero and low-pyruvate structures (variants 1 and 2), the strain that produces them and the process for production of the polymer.

U.S. Pat. No. 6,316,614 discloses all 6 variants, the strains that produce them and the process for production of the polymers.

Fermentation Process

The degree of pyruvylation appears to be particularly sensitive to the fermentation conditions and media. In particular the nitrogen source and oxygen availability have been shown to have an effect on pyruvate content. Peters et al. showed that the degree of pyruvylation decreased when the microbial oxygen demand was not met (Peters, H.-U., Suh, I.-S., Schumpe, A. and Deckwer, W.-H. "The pyruvate content of xanthan polysaccharide produced under oxygen limitation." *Biotechnology Letters*, 15 (1993) 565-566). Flores Candia and Deckwer (cf. above) demonstrated that the pyruvate level was dependent on the level of $NH_4Cl$ in the fermentation media. They found that pyruvate content increased with decreasing nitrogen content in the media.

For example, at 8.4 g/l $NH_4Cl$, the pyruvate content remained constant at approximately 1.5% throughout the 140 h fermentation but at lower nitrogen levels (0.62 g/l) the pyruvate content came close to the theoretical maximum. The preparation of a high pyruvate xanthan gum through the control of the nitrogen content in the fermentation media is the subject of U.S. Pat. No. 4,394,447. The patent defines high pyruvate as at least 3.3% pyruvic acid by weight measured by an enzymatic method. This patent only discusses the fermentation conditions and no disclosure relates to the functionality or application of a high pyruvate xanthan gum.

Post Fermentation Treatment

Heat treatment of the fermentation broth at acidic pH's prior to recovery favours the removal of pyruvate groups. Heat treatment of the fermentation broth at alkaline pH prior to recovery favours the removal of acetate groups. Acetate can also be removed by treatment with alkali under nitrogen at room temperature.

Commercial Potential of Modified Xanthan

Commercially available xanthan products in which the acetate or pyruvate content has been deliberately controlled are available. CPKelco produces acetate-free products for food and non-food use called KELTROL ASX and KELZAN ASX, respectively. The main functionality benefit for this type of products is seen primarily in very strong acidic systems such as toilet cleaners where up to 5 to 10% strong acids are used giving the products a pH of around pH 2 or below. Significantly better long term stability is seen with the low acetate xanthan compared to a conventional product. In less acidic food products such as food dressings, the differences are much less significant. This product has greater synergy with galactomannans compared to standard xanthan and higher low shear viscosity than standard products. The product is made using a *Xanthomonas* strain that does not add the acetate group during fermentation (U.S. Pat. No. 6,316,614 B1).

To conclude, there is still a need to provide improved xanthan gums, in particular xanthan gums with improved rheological and/or synergy properties.

OBJECT OF THE INVENTION

It is an object of embodiments of the invention to provide improved xanthan gums and means and methods for their production.

SUMMARY OF THE INVENTION

It has been found by the present inventors that xanthan gum produced by *Xanthomonas campestris* strain CFBP 176 has a very high content of pyruvic acid compared to xanthan gum from other *X. campestris* strains. Further it has been found that this particular xanthan gum can be prepared by a combination of process steps which provides for a number of attractive functional properties, including excellent solution rheology properties as well as synergy in admixture with galactomannans and glucomannans.

So, in a first aspect the present invention relates to a xanthan gum having the following characteristics
- a pyruvic acid content of at least 5.0% (w/w)
- a pyruvic acid to acetic acid w/w ratio of at least 0.5
- a low shear viscosity measured at 0.3% gum in 1% NaCl at a shear rate of 0.01 $s^{-1}$ at 23±2° C. of at least 80 Pa·s.

In a second aspect, the invention relates to a method for preparing a xanthan gum, comprising culturing a *Xanthomonas campestris* strain or a derivative or progeny thereof in a culture medium under conditions facilitating xanthan gum production by said strain or derivative or progeny, subjecting the culture medium to heat treatment and subsequently recovering the xanthan gum from said culture medium.

In a third aspect, the present invention relates to a composition comprising a xanthan gum of the invention, or prepared according to the method of the invention, in admixture with at least one galactomannan or glucomannan.

In a fourth aspect, the invention relates to a food or feedstuff product comprising a xanthan gum of the invention, a xanthan gum produced according to the process of the invention, or a composition of the invention.

Finally, the invention also relates the use of *Xanthomonas campestris* strains CFBP 19, CFBP 176, CFBP 64, CFBP 412, ATCC 17915, ATCC 19046, or CFBP 1847, or use of a derivative or progeny of any one of strains CFBP 19, CFBP 176, CFBP 64, CFBP 412, ATCC 17915, ATCC 19046, and CFBP 1847 for the production of high viscosity and high synergy xanthan gum.

LEGENDS TO THE FIGURE

Figure 1:
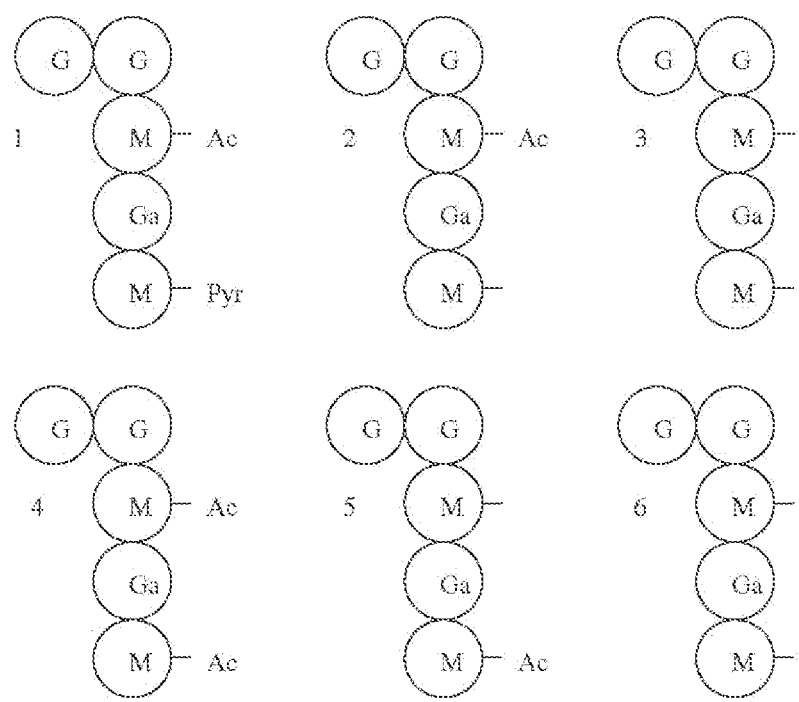

FIG. 1: Schematic depiction of the repeating structural unit of xanthan based polymers from mutant strains of *Xanthomonas campestris*.

FIG. 2: Structural formula of the repeating units of xanthan based polymers.

Figure 3:
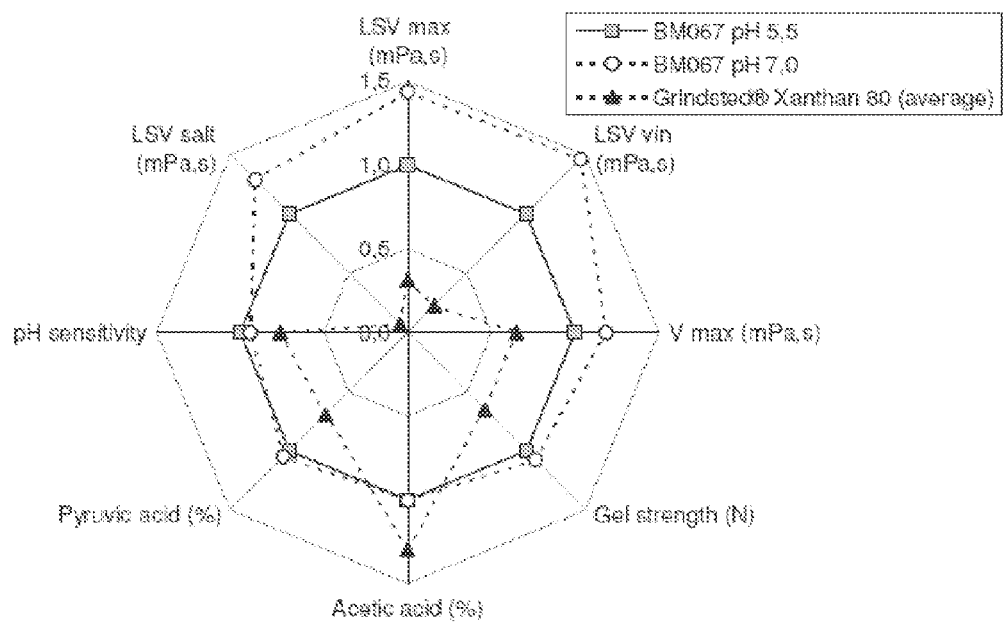

FIG. 3: Spider graphs showing a comparison of the functionality of xanthan from strain CFBP 176 produced at pilot scale with the average value for a standard commercial xanthan gum.

Figure 4:
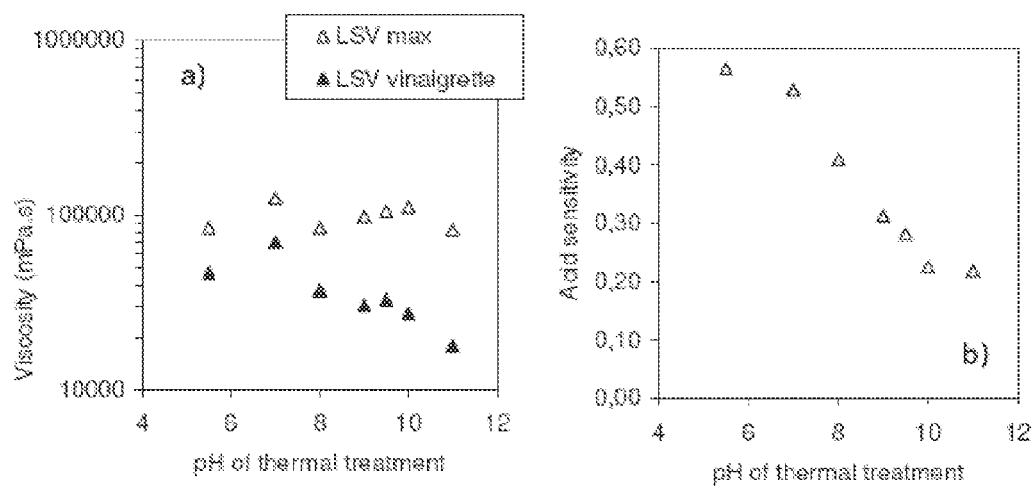

FIG. 4: Graphs showing the effect of the pH of thermal treatment at 120° C. on a) $LSV_{max}$ and $LSV_{vinaigrette}$ and b) pH sensitivity of xanthan from strain CFBP 176.

Figure 5:
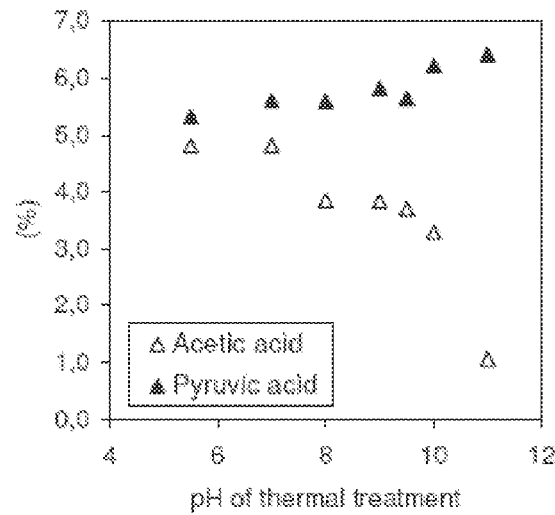

FIG. 5: Graph showing the effect of the pH of the thermal treatment at 120° C. on the substituent groups of xanthan from strain CFBP 176.

Figure 6:
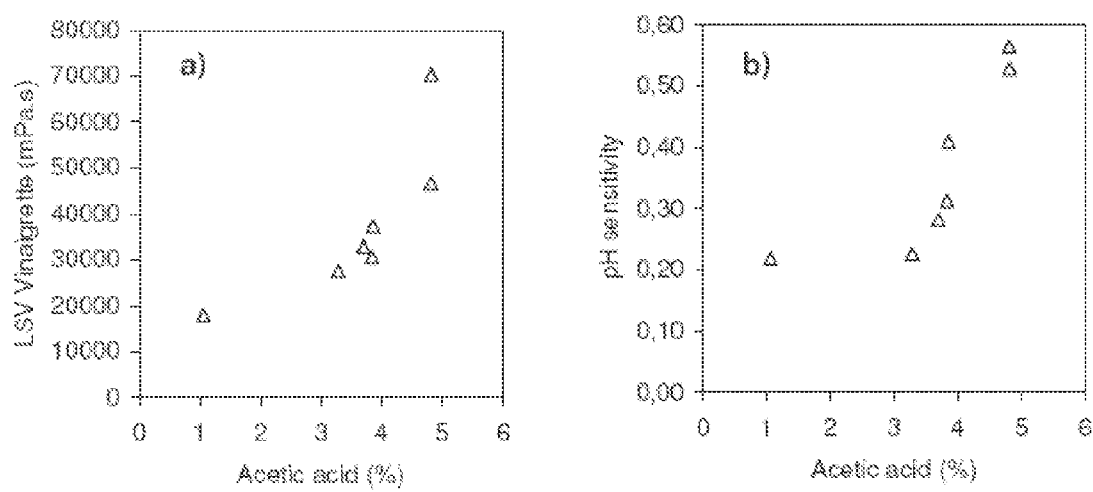

FIG. 6: Graphs showing the effect of the acetic acid content on a) LSV vinaigrette and b) acid sensitivity of xanthan produced from strain CFBP 176.

Figure 7:
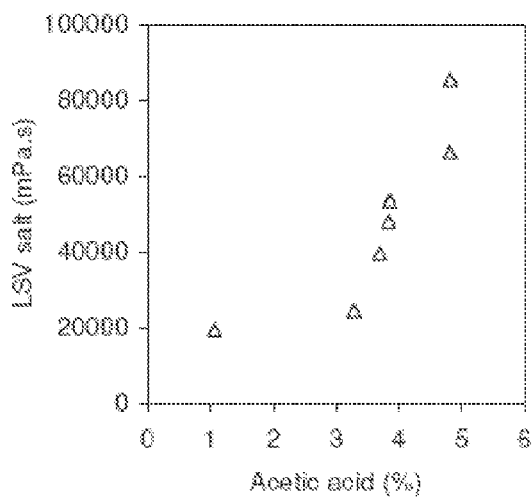

FIG. 7: Graph showing the effect of acetic acid content of xanthan produced from CFBP 176 on the $LSV_{salt}$ viscosity.

Figure 8:
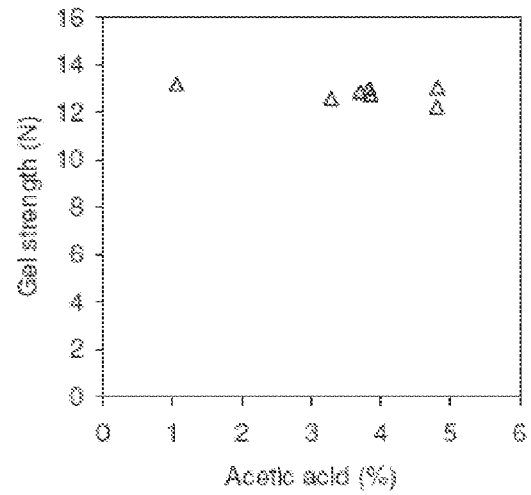

FIG. 8: Graph showing the effect of acetic acid content of xanthan gum produced from strain CFBP 176 on the gel strength of 1% 1:1 Xanthan:LBG gels.

Figure 9:
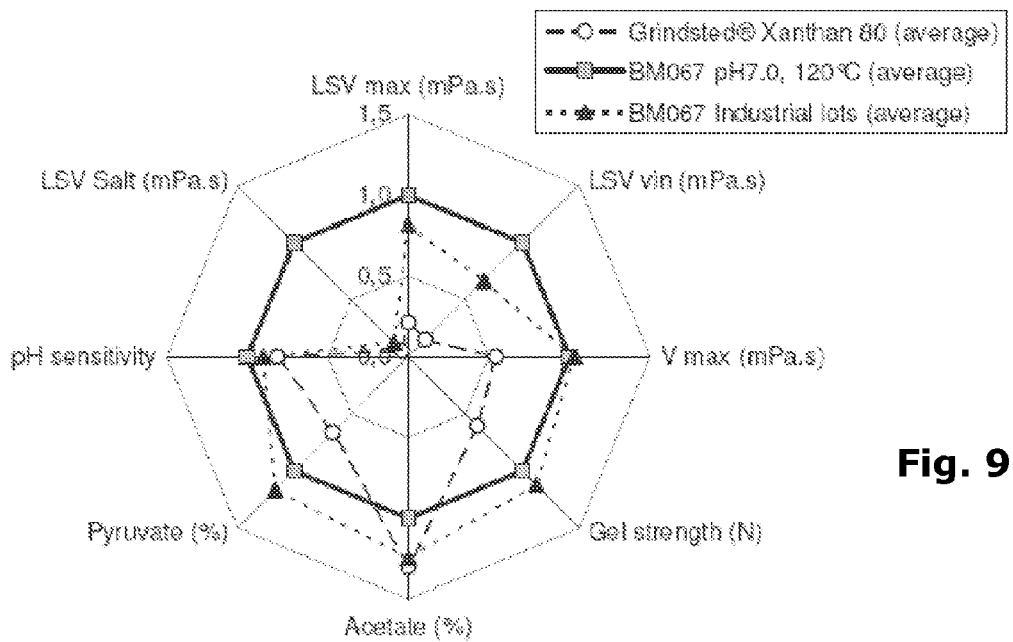

FIG. 9: Graph showing the comparison of the functionality of xanthan from CFBP 176 produced at industrial and pilot scale with the average value for a standard commercial xanthan gum.

Figure 10:
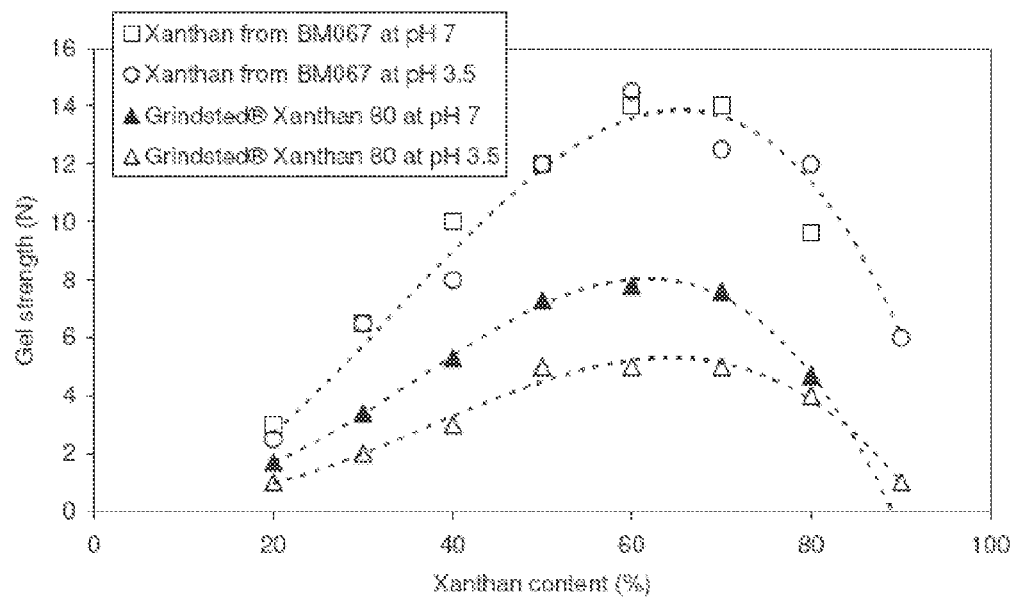

FIG. 10: Graph showing the gel strength as a function of xanthan/LBG ratio for 1% total gum in 0.5% NaCl at pH 7 and pH 3.5, respectively.

Figure 11:
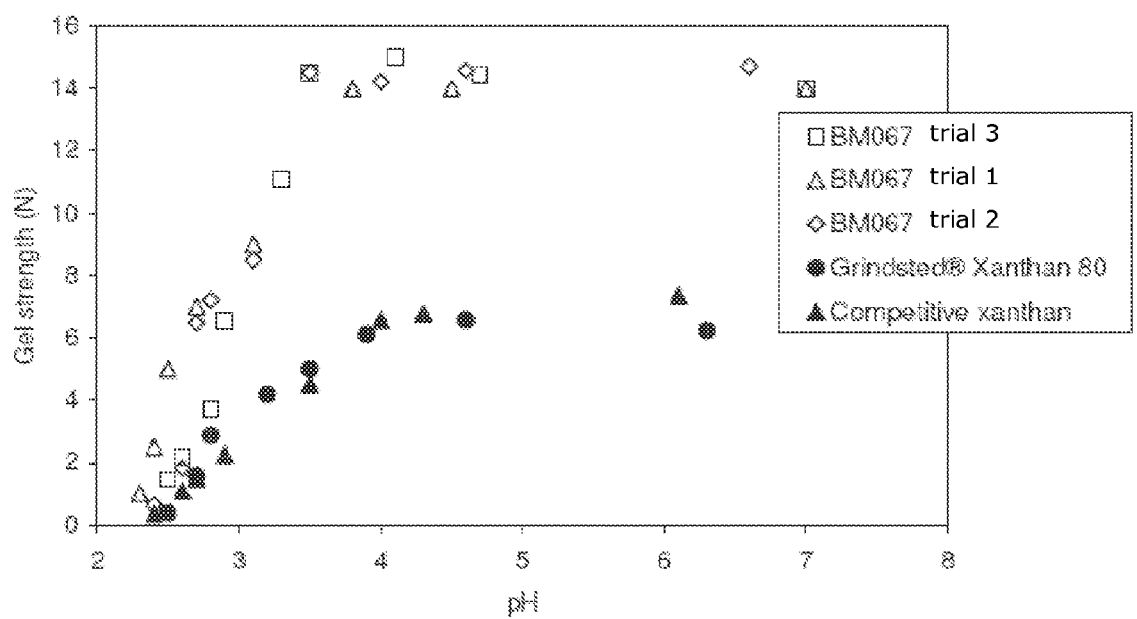

FIG. 11: Graph showing the gel strength as a function of pH for 60/40 xanthan/LBG gels at 1% total gum in 0.5% NaCl.

Figure 12:
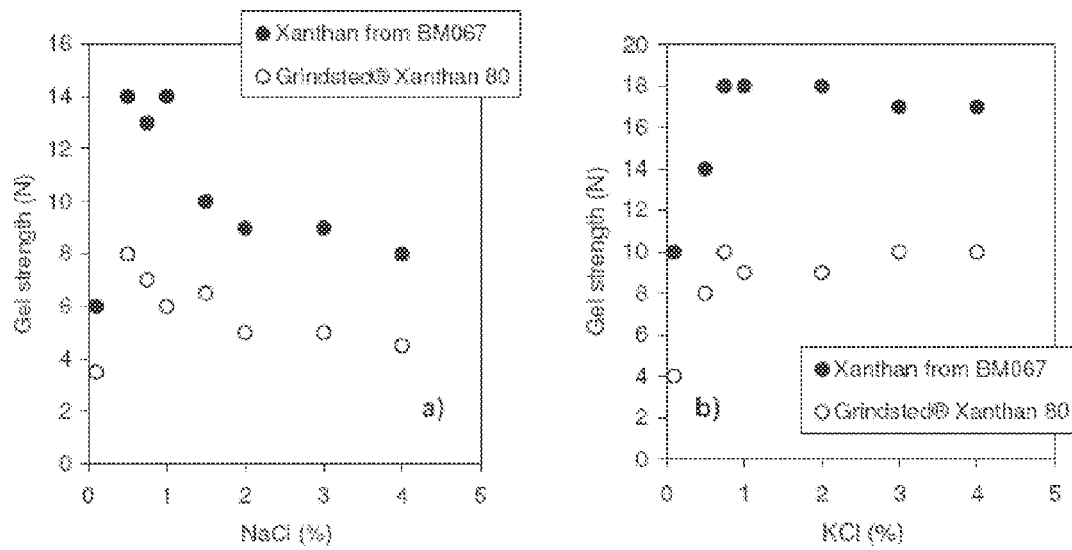

FIG. 12: Graphs showing the effect of a) NaCl and b) KCl on the gel strength of xanthan/LBG 60/40 gels at 1% total gum.

Figure 13:
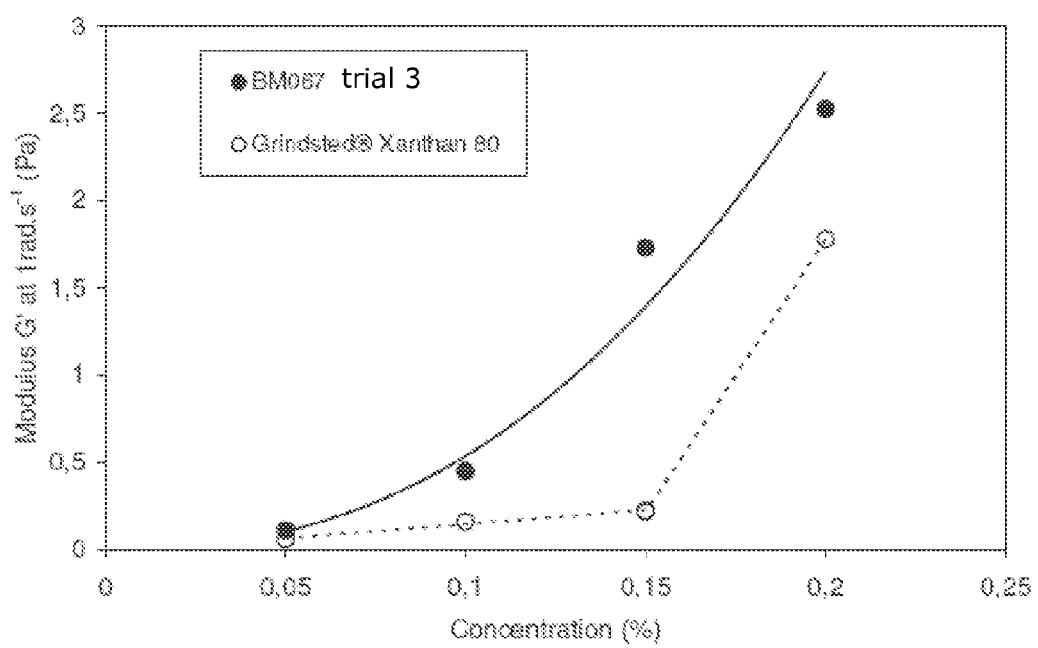

FIG. 13: Graph showing the elastic modulus, G', as a function of gum concentration for a 60:40 mixture of xanthan: LBG in a vinaigrette formulation (1% NaCl, pH 2.5).

Figure 14:
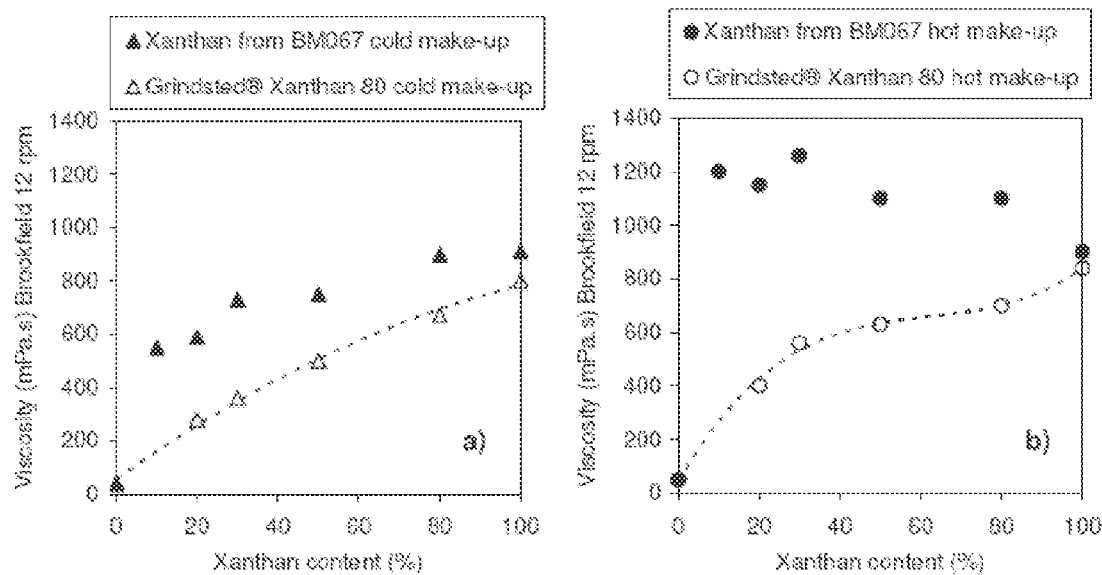

FIG. 14: Graph showing the effect of xanthan/guar ratio on the viscosity after a) cold make up and b) hot make up (0.3% total gum in 1% NaCl).

Figure 15:
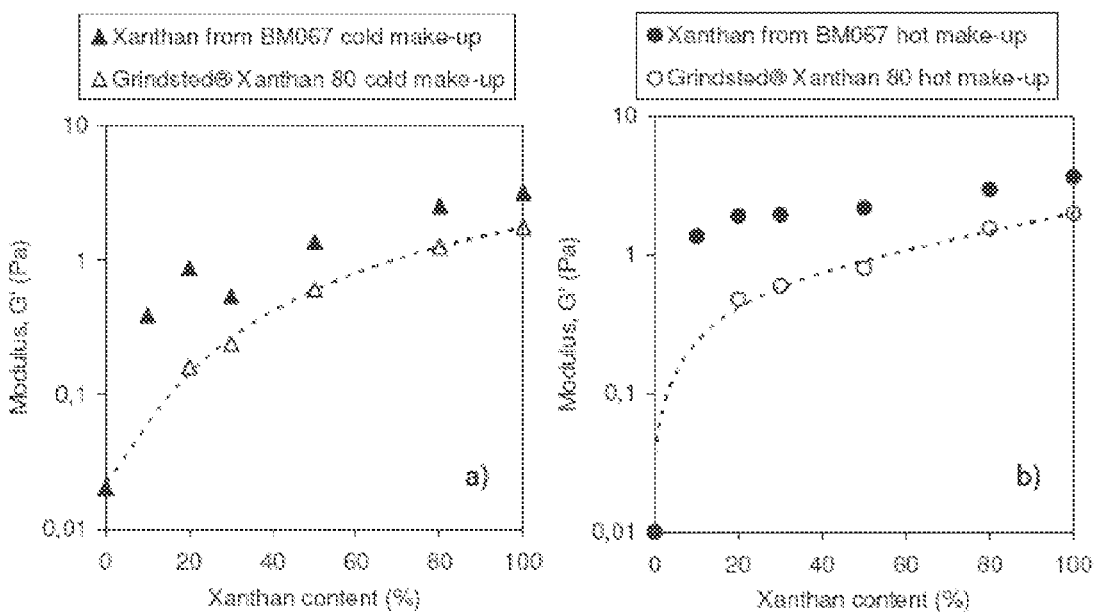

FIG. 15: Graph showing the effect of xanthan/guar ratio on the elastic modulus at 1 rad·s$^{-1}$ after a) cold make up and b) hot make up (0.3% total gum in 1% NaCl).

Figure 16:
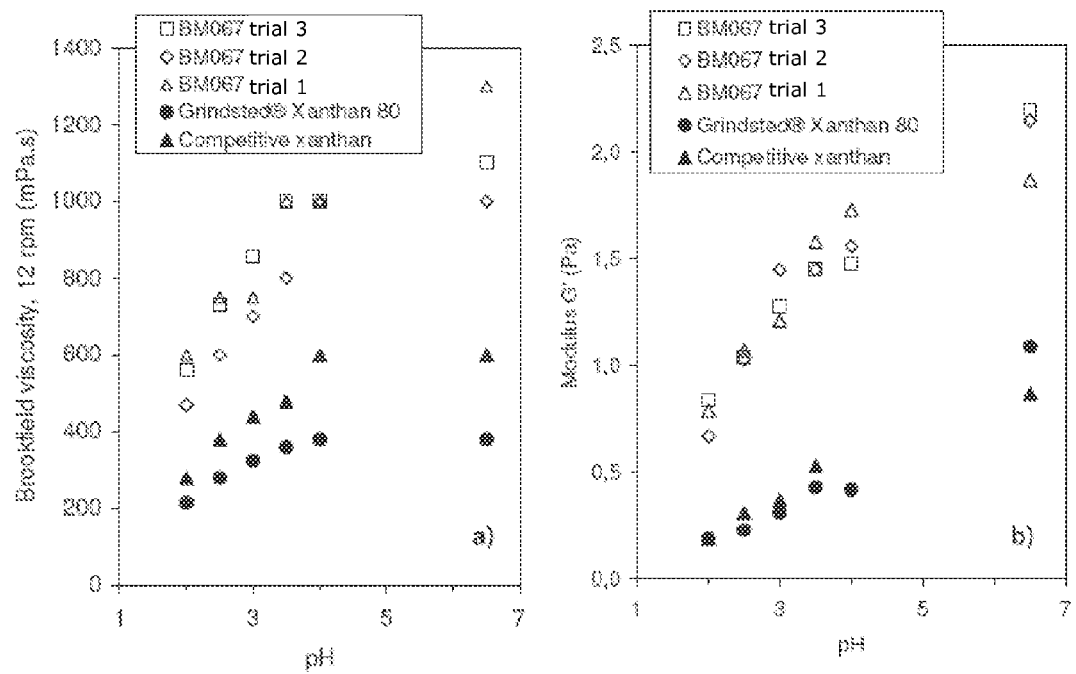

FIG. 16: Graph showing the effect of pH on a) Brookfield viscosity at 12 rpm and b) Elastic modulus at 1 rad·s$^1$ of 50:50 mixtures of xanthan:guar at 0.3% total gum in 9% sucrose+ 1% NaCl.

Figure 17:
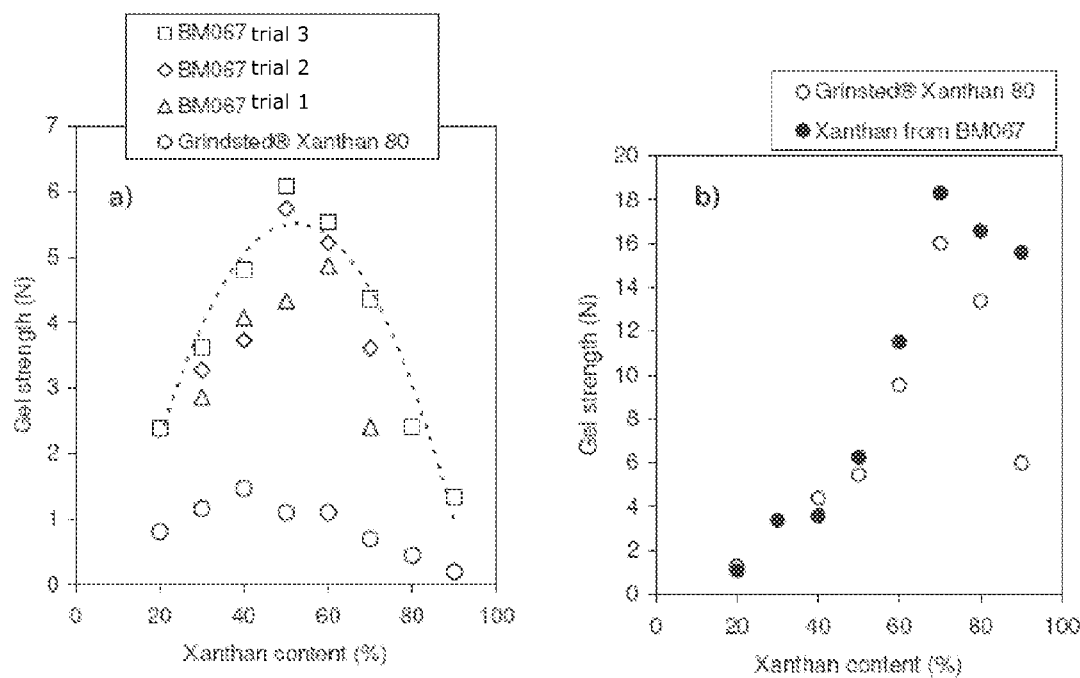

FIG. 17: Graph showing the effect of gum ratio on the gel strength of a) xanthan/tara and b) xanthan/konjac at 1% total gum in 0.5% % NaCl.

Figure 18:
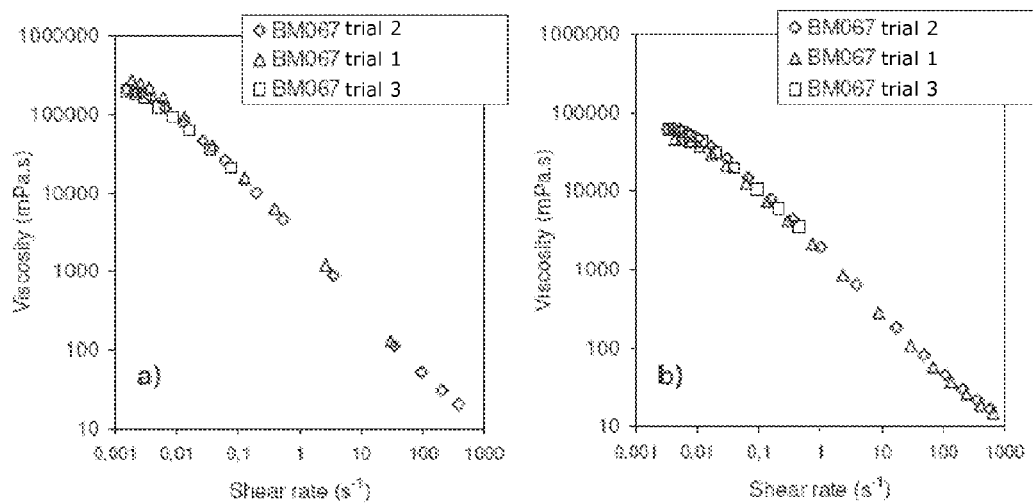

FIG. 18. Graph showing the flow viscosity of industrial lots of CFBP 176 at 0.3% in a) 1% NaCl and b) 1% NaCl, pH 2.5. 0,001 0,01 0,1 1 10 Shear rate (s−1).

Figure 19:
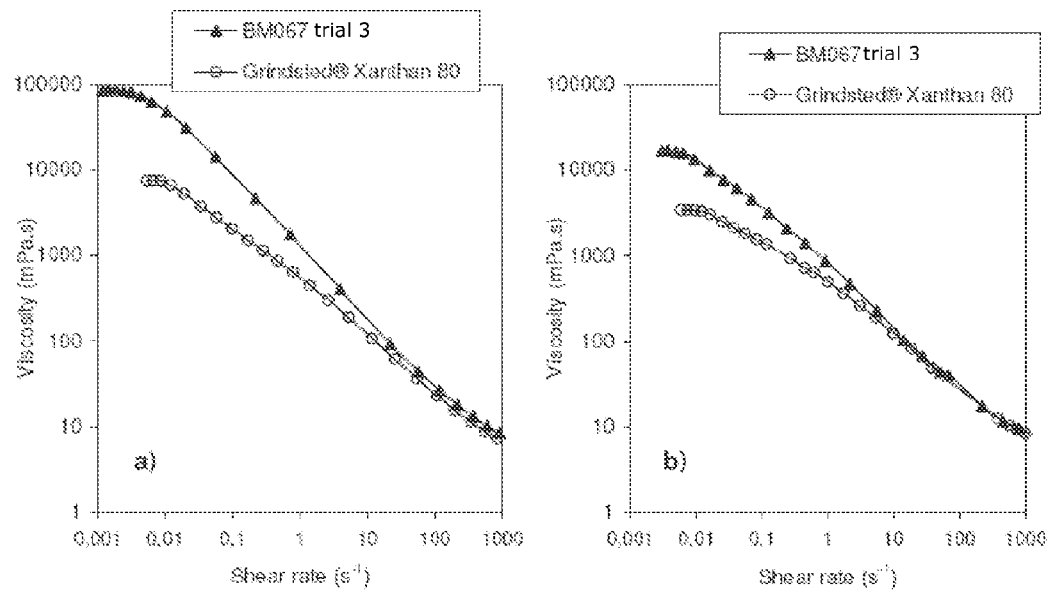

FIG. 19: Graph showing the flow viscosity of 0.2% xanthan in a) 1% NaCl and b) 1% NaCl, pH 2.5.

Figure 20:
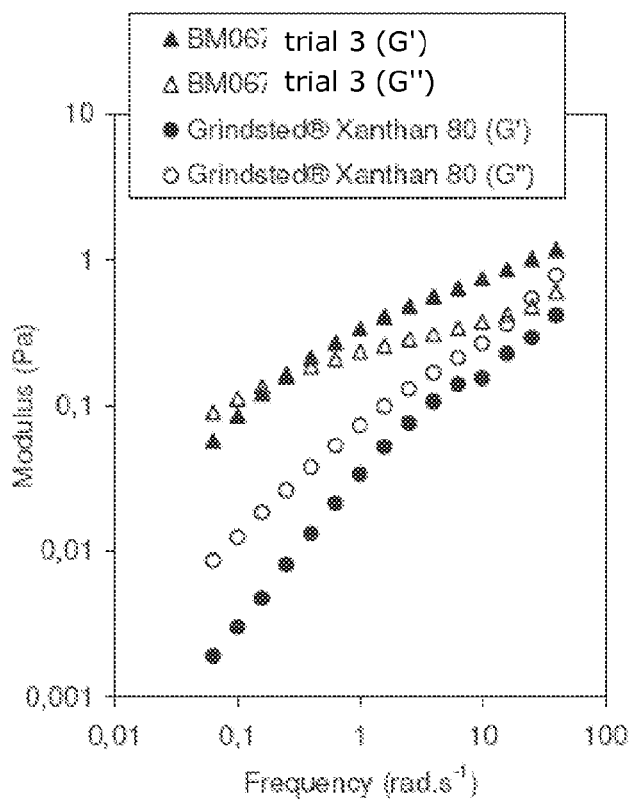

FIG. 20: Graph showing the viscoelastic profile of 0.1% xanthan in 1% NaCl.

Figure 21:
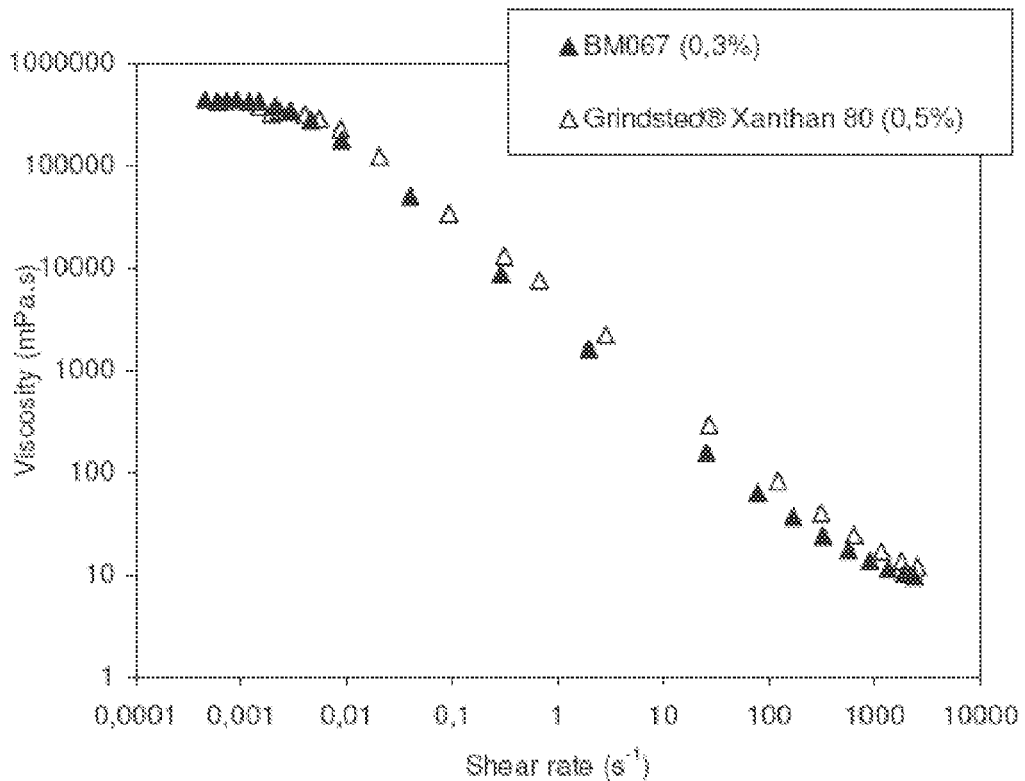

FIG. 21: Graph showing the flow viscosity of xanthan in 1% NaCl.

Figure 22:
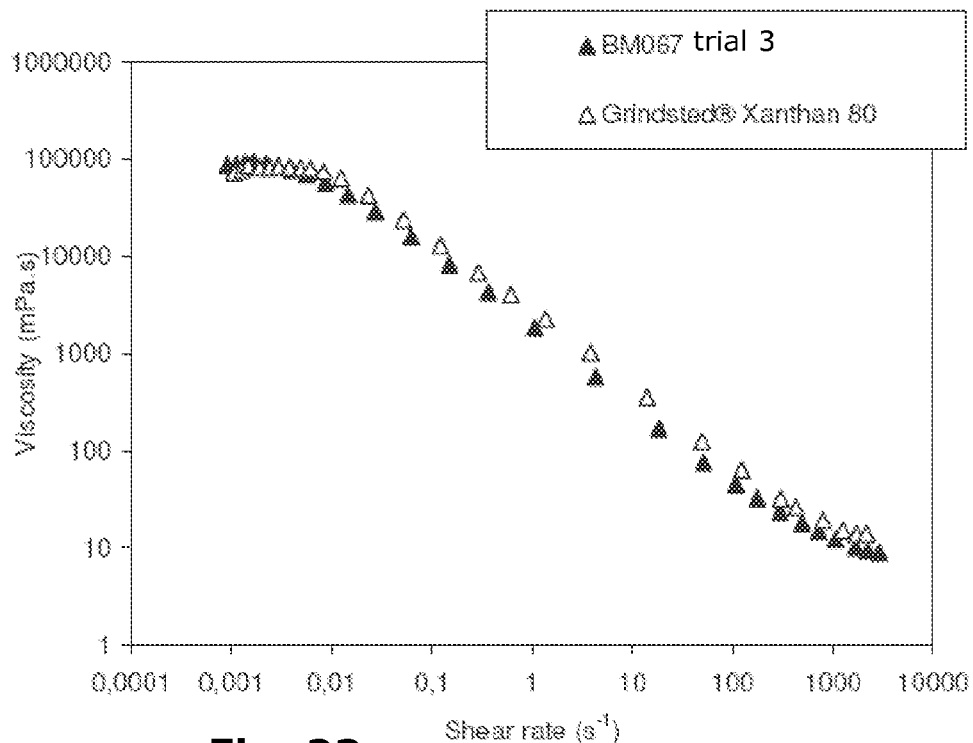

FIG. 22: Graph showing the flow viscosity of xanthan in 1% NaCl at pH 2.5.

Figure 23:
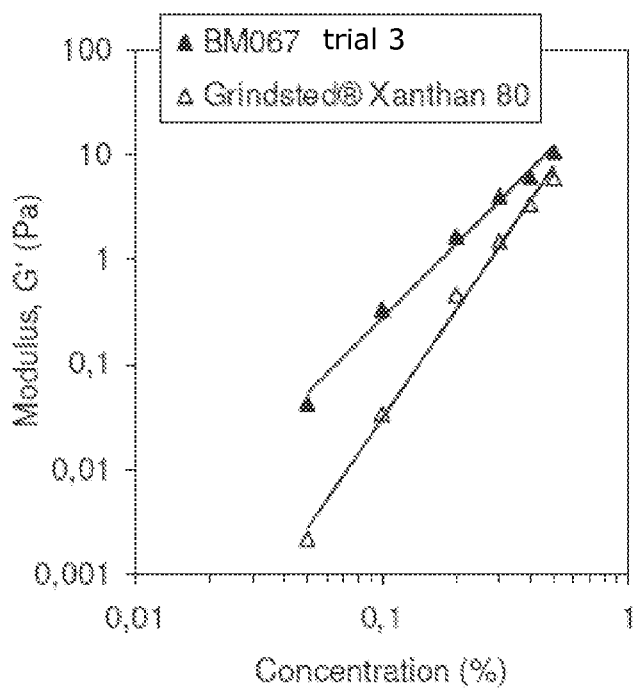

FIG. 23: Graph showing the elastic modulus (G') as a function of xanthan gum concentration in 1% NaCl (measured at 1 rad·s$^{-1}$).

Figure 24:
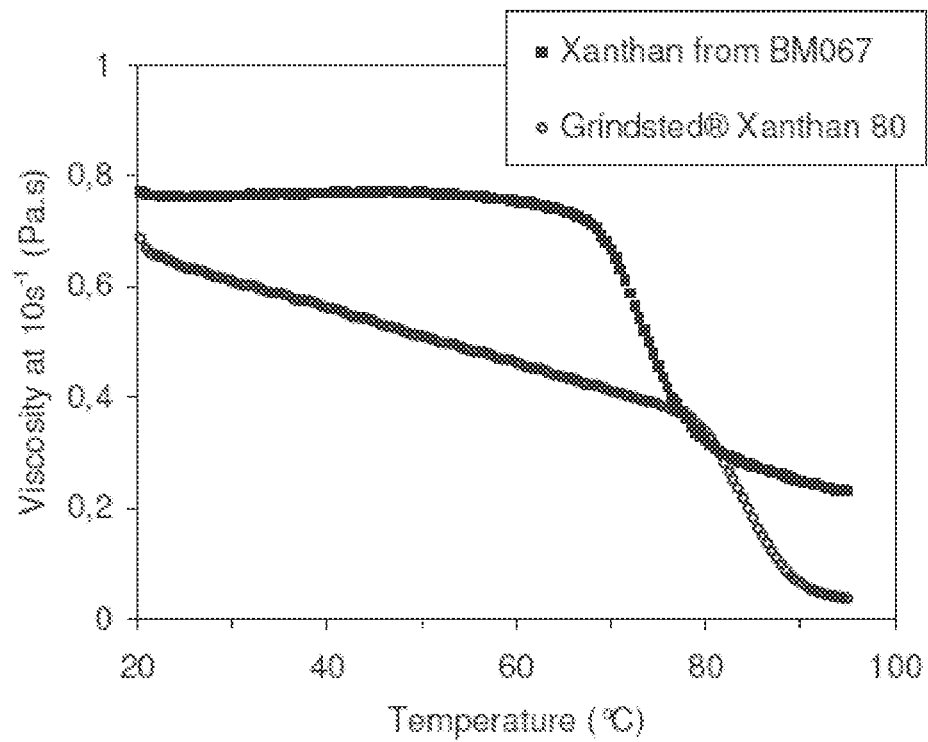

FIG. 24: Graph showing the conformational transition of xanthan gum as measured by viscosity (0.5% xanthan in 0.2% NaCl measured at 10 s$^{-1}$).

Figure 25:
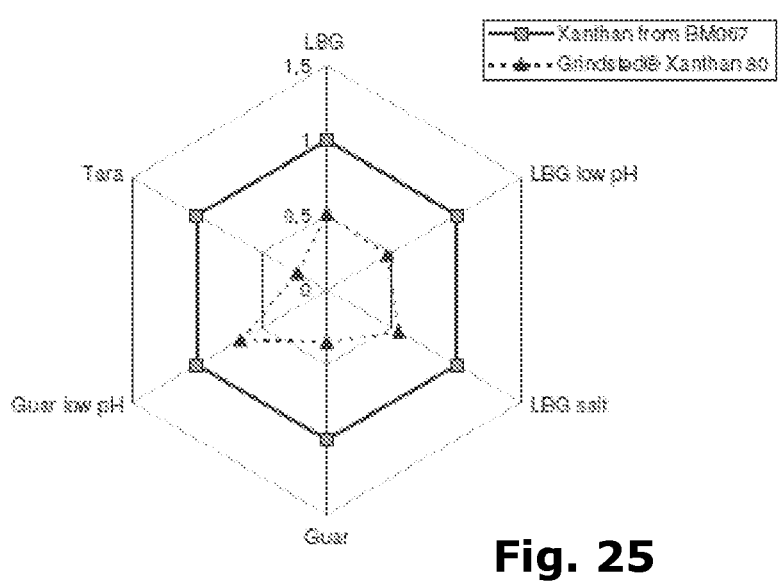

FIG. 25: Spider graph showing a comparison of the galactomannan synergy of CFBP 176 with that of Grindsted® Xanthan 80.

Figure 26:
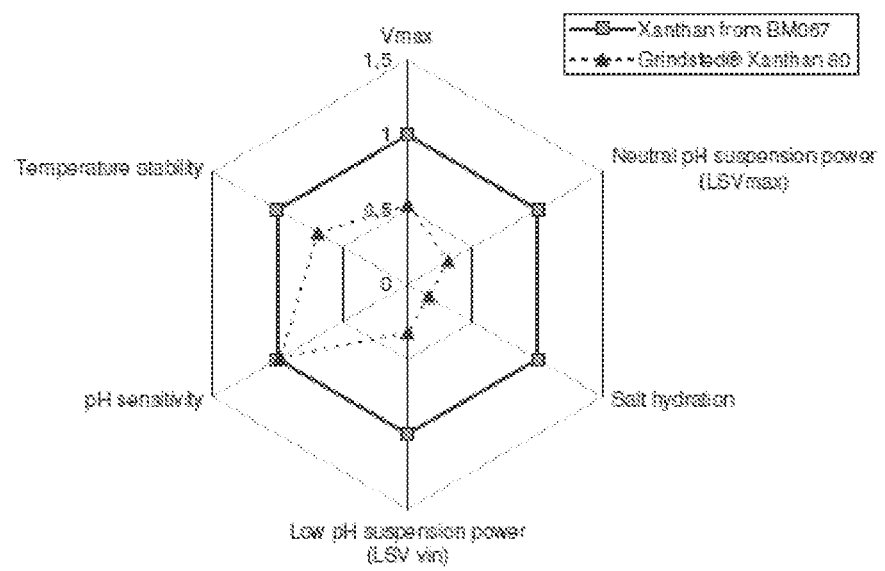

FIG. 26: Spider graph showing a comparison of the rheological properties of CFBP 176 with those of Grindsted® Xanthan 80.

DETAILED DISCLOSURE OF THE INVENTION

Definitions

A *Xanthomonas campestris* strain (or *X. campestris* strain) is a strain of the bacterial species which causes a variety of plant diseases. *X. campestris* is used in the commercial production of the high molecular weight polysaccharide xanthan gum that is an efficient viscosifier of water and that has many important uses, especially in the food industry.

A "derivative" of a *X. campestris* strain is in the current context a bacterial cell which is derived from *X. campestris*, where said bacterial cell has preserved substantially all genomic information of the *X. campestris* strain—the derivative may, however, differ from the parent *X. campestris* strain by having recombinantly introduced genetic modifications (e.g. in the genome or in the form of a plasmid), which do not adversely affect the functionality of the xanthan gum gene cluster.

A "progeny" of a *X. campestris* strain is a bacterial cell which is obtained by culture of a *X. campestris* strain—hence, the progeny may include later generation bacterial cells which are not genetically identical with the original *X. campestris* strain (due, e.g., to the emergence of natural recombination events, or spontaneous mutations), but which do not include any genetic changes which adversely affect the functionality of the xanthan gum gene cluster.

A *X. campestris* strain producing xanthan gum having a high pyruvic acid content is a strain which produces Xanthan gum having a pyruvic acid content of at least 5%.

When discussing viscosity and gel strength of compositions comprising xanthan gums, these parameters are generally determined by use of the methods and apparatus specifically referred to in the examples. For example, viscosity expressed as $V_{max}$ is generally measured using a Brookfield LVT dial reading viscometer at the indicated spindle speed (typically 1.5 rpm).

1$^{st}$ Aspect of the Invention

The first aspect of the invention relates to a xanthan gum having at least the following characteristics a pyruvic acid content of at least 5.0% (w/w)

a pyruvic acid to acetic acid w/w ratio of at least 0.5 a low shear rate viscosity ($LSV_{max}$) measured at 0.3% gum in 1% NaCl at a shear rate of 0.01 s$^{-1}$ at 23±2° C. of at least 80 Pa·s.

In the present specification and claims, all measurement values are obtained at at 23±2° C. unless other temperatures are indicated.

The pyruvic acid content may be higher, e.g. at least 5.3% (w/w), but higher values are preferred such as at least 5.6% (w/w).

It is further preferred that the pyruvic acid to acetic acid w/w ratio in the xanthan gum is higher, e.g. at least 0.6, at least 0.7, at least 0.8, at least 0.9, and at least 1.0. It is in particular preferred that this ratio is about 1.1.

The xanthan gums of the present invention exhibit particularly good rheological properties. It has e.g. been found that the low shear viscosity ($LSV_{max}$) values observed for the inventive xanthan gums are superior to those of existing commercial products—the main advantage derivable from this property of the inventive xanthan gums is that the amount of xanthan gum may be reduced while retaining product stability and texture compared to a product containing the existing marketed xanthan gums.

In one embodiment of the invention, the xanthan gum has a low shear viscosity ($LSV_{max}$) measured at 0.3% xanthan in 1% w/v NaCl at a shear rate of 0.01 s$^{-1}$, which is at least 90 Pa·s. In another embodiment the $LSV_{max}$ measured at 0.3% xanthan in 1% w/v NaCl at a shear rate of 0.01 s$^{-1}$ is in the range from 90-130 Pa·s, such as in the range from about 95 to about 125 Pa·s.

In a further embodiment, the xanthan gum of the invention has a low shear viscosity measured at 0.3% gum at a shear rate of 0.01 s$^{-1}$ in 1% w/v NaCl and vinegar (12°) at pH=2.5 of at least 18 Pa·s. However, in other embodiments of the invention, this value is higher, such as at least 20, at least 25, at least 30, at least 35, and at least 40 Pa·s.

In yet a further embodiment, the xanthan gum of the invention has a low shear viscosity at a shear rate of $0.01\ s^{-1}$ in 2.5% w/v NaCl of at least 6 Pa·s. However, in other embodiments of the invention, also this value is higher, such as at least 7, at least 8, and at least 9. Further, since the pilot scale tests reported in the examples below achieved considerably higher viscosities in 2.5% NaCl, it is contemplated that the low shear viscosity at a shear rate of $0.01\ s^{-1}$ in 2.5% w/v NaCl will be at least 20, such as at least 30, at least 40, or at least 50 Pa·s.

The feature of improved synergy with galactomannans such as with locust bean gum is also a very prominent and important feature of the present invention, which allows for the preparation of products where the amount of xanthan gum and/or galactomannan may be reduced without impeding the properties of the combined products.

Hence, embodiments of the invention relates to the xanthan gums of the invention, which exhibit a gel strength (Synergy Test) with locust bean gum (LBG) measured at 1% gum (60:40 Xanthan/LBG) in 1% KCl of at least 13.0 N, such as at least 13.1, 13.2, 13.3, 13.4, 13.5, 13.6, 13.7, 13.8, 13.9 and at least 14 N.

As will appear from the examples, an exemplary xanthan gum of the invention is prepared by fermentation of *X. campestris* CFBP 176 (*X. campestris juglandis*), which was initially selected due to the high pyruvic acid content in the xanthan gum. However, it is expected that it is possible to provide equally good xanthans having the same or at least comparable solution rheology and synergy properties by preparing xanthan gums from other *X. campestris* strains, which are known to or can be demonstrated to produce xanthan gums having a high pyruvate content. According to the invention, the xanthan gum of the invention may hence be produced by strains selected from the following *Xanthomonas campestris* strains (the first column refers to the nomenclature used in the figures):

| Melle Code RTAM | Name | Origin |
| --- | --- | --- |
| BM065 | campestris cynarae | CFBP 19 |
| BM067 | campestris juglandis | CFBP 176 |
| BM068 | campestris pelargonii | CFBP 64 |
| BM116 | campestris phaseoli | CFBP 412 |
| BM120 | campestris phaseoli | ATCC 17915 |
| BM213 | campestris celebenois | ATCC 19046 |
| BM282 | campestris corylina | CFBP 1847 | where the origin column refers to the deposit number with the American Type Culture Collection (10801 University Boulevard, Manassas, Va. 20110-2209, USA) or with Collection Francaise de Bactéries Phytopathogénes (42, rue G. Morel, Beaucouze, BP 60057, 49071, France).

Accordingly, in embodiments of the invention, the xanthan gum is a product of a *Xanthomonas campestris* strain selected from the group consisting of strains CFBP 19, CFBP 176, CFBP 64, CFBP 412, ATCC 17915, ATCC 19046, and CFBP 1847, or is a product of a derivative or progeny of any one of strains CFBP 19, CFBP 179, CFBP 64, CFBP 412, ATCC 17915, ATCC 19046, and CFBP 1847.

As will be apparent from the examples, the xanthan gum of the invention exhibits a number of advantageous functional properties, which all are considered important embodiments of the invention; this is particular the case for the synergistic properties when admixed with various galatomannans and glucomannans.

For example, one embodiment relates to a xanthan gum of the invention, which exhibits a gel strength in a gel comprising 1% gum comprised of 60/40 xanthan/LBG at pH 7 in 0.5% NaCl of at least 10N—higher values are preferred, such as at least 10.5N, at least 11N, at least 11.5N at least 12N, at least 12.5N, at least 13N, and at least 13.5N. It is especially preferred that the gel strength is in the range between 13 and 15 N, e.g. about 14N. It is generally found that the inventive xanthan exhibits higher gel strength in admixture with LBG than any existing commercially available xanthan gum and at all xanthan/LBG ratios.

It is noted that all measurements of gel strength are performed as described in the Examples.

In a different embodiment, the xanthan gum of the invention exhibits a gel strength in a gel comprising 1% gum comprised of 60/40 xanthan/LBG at pH 3.0 in 0.5% NaCl of at least 8N. Again, higher values are preferred, such as at least 8.5N, at least 9.0N, at least 9.5N, and at least 10N. It is preferred that the gel strength under these conditions is in the range 9-11N.

In yet another embodiment, the xanthan gum of the invention exhibits a gel strength in a gel comprising 1% gum comprised of 60/40 xanthan/LBG at pH 7.0 in 2% NaCl of at least 8N., such as at least 8.5 N and at least 9.0 N. A preferred range is between 9 and 10N.

An embodiment of the xanthan gum of the invention exhibits a viscosity in a gel comprising 0.3% gum comprised of 80/20 guar/xanthan at pH 7.0 in 1% NaCl of at least 400 mPa·s when measured with a Brookfield LVT at 12 rpm. The viscosity is preferably higher, e.g. at least 500, at least 600, at least 700, at least 800, at least 900, at least 1000, and at least 1100 mPa·s. A preferred range is between 1000 and 1300 mPa·s, e.g. about 1200 mPa·s.

Another embodiment of the xanthan gum of the invention exhibits a viscosity in a gel comprising 0.3% gum comprised of 50/50 guar/xanthan at pH 3.0 in 1% NaCl and 9% sucrose of at least 500 mPa·s when measured with a Brookfield LVT at 12 rpm. The viscosity is preferably higher, such as at least 550, at least 600, at least 650, and at least 700 mPa·s. A preferred range is between 650 and 800 mPa·s, e.g. about 800 mPa·s.

An embodiment of the xanthan gum of the invention exhibits a gel strength in a gel comprising 1% gum comprised of 50/50 xanthan/tara at pH 7.0 in 0.5% NaCl of at least 2.5N, but higher values are preferred—for instance the gel strength is at least 3N, and at least 4N, with a preferred range between 4 and 6N.

However, the xanthan of the invention also exhibits advantageous properties in isolation: An embodiment of the xanthan gum of the invention exhibits a viscosity measured with a Brookfield LVT viscometer as a $V_{max}$ of 0.3% xanthan in 1% NaCl at 1.5 rpm of at least 5000 mPa·s. Higher $V_{max}$ values are preferred such as at least 5100, at least 5200, at least 5300, at least 5400, at least 5500, at least 5600, at least 5700, at least 5800, at least 5900, at least 6000, and at least 6100 mPa·s. The preferred range is between 6200 and 6800 mPa·s.

Another embodiment of the xanthan gum of the invention exhibits a viscosity ($LSV_{salt}$) at $0.01\ s^{-1}$ of 0.3% xanthan after 30 minutes hydration in 2.5% NaCl, pH 2.5 at 500 rpm of at least 5000 mPa·s. Again, higher values are preferred, such as at least 5500, at least 6000, at least 6500, and at least 7000. As shown in the pilot trials referenced in the Examples, considerably higher values can be obtained with the xanthans of the present invention, so it is contemplated that the $LSV_{salt}$ may reach values of at least 50000, such as at least 60000, at least 65000, at least 70000, at least 75000, and at least 80000, with a preferred range between 75000 and 90000 mPa·s.

Finally, an embodiment of the xanthan of the invention exhibits a high temperature stability as expressed as the ratio between the viscosities at 60° C. and 20° C. (measured on 0.2% xanthan gum in 0.5% NaCl at a shear rate of 10 s$^{-1}$). In embodiments of the invention, this ratio exceed 0.75, but may be higher, such as at last 0.80, at least 0.85, at least 0.90, and at least 0.95. It is preferred that this ratio is in the range 0.9 to 1.0, and values about 1 are preferred (meaning that the viscosity is not sensitive to temperatures up to 60° C.

2$^{nd}$ Aspect of the Invention

It has been found by the present inventors that a number of specific process steps performed with post-fermentation products of *Xanthomonas campestris* provide for improved xanthan gums, when the *X. campestris* strain provides for xanthan gum having high pyruvic acid content.

The second aspect of the invention relates to a method for preparing xanthan gum of the first aspect of the invention, comprising culturing a *Xanthomonas campestris* strain, which produces xanthan gum having a high pyruvic acid content, or a derivative or progeny thereof, in a culture medium under conditions facilitating xanthan gum production by said strain or derivative or progeny, subjecting the culture medium to heat treatment and subsequently recovering the xanthan gum from said culture medium.

In one embodiment, the *Xanthomonas campestris* strain is any one of the strains discussed above.

Typically, the heat treatment is performed at a temperature in the range 100-130° C., such as in the range from 105-125° C. In one embodiment of the invention, the temperature in the heat treatment is about 120° C.

It has also been found that the pH during the heat treatment influences the characteristics of the xantham gum produced. In one embodiment the heat treatment is performed at a pH in the range between 5.5 and 11.0, such as in the range between 6 and 9, e.g. in the range between 6.5 and 8.

In one interesting embodiment, the pH is about 7.

It will be understood from the present application that the present inventors also have identified the advantageous use of any of the above-discussed *Xanthomonas campestris* strains or of a derivative or progeny thereof for the production of high viscosity xanthan gum.

3$^{rd}$ Aspect of the Invention

As shown herein, the xanthan gums of the invention and the xanthan gums produced according to the method of the invention exhibit a series of advantageous properties when admixed with other gelling agents.

Hence, an embodiment of the invention relates to a composition comprising a xanthan gum of the first aspect of the invention or prepared according to the second aspect of the invention, in admixture with at least one galactomannan or glucomannan. Typically, the at least one galactomannan is selected from the group consisting of guar gum, tara gum, locust bean gum, cassia gum, and typically, the glucomannan is konjac glucomannan.

In embodiments of the third aspect, the composition according further comprises a salt, such as an inorganic salt, e.g. NaCl or KCl or CaCl$_2$.

In embodiments of the third aspect, the weight ratio between the xanthan gum and the at least one galactomannan or glucomannan is at least 5:95, such as at least 10:90, at least 15:85, at least 20:80, at least 25:75, at least 30:70, at least 35:65, at least 40:60, at least 45:55, at least 50:50, at least 55:45, at least 60:40, at least 65:35, at least 70:30, at least 75:25, at least 80:20, at least 85:15, at least 90:10, at least 95:5 (however any ratio, where the inclusion of the xanthan gum provides an improvement over the use of the galactomannan and glucomannan alone). On the other hand, the weight ratio between the xanthan gum and the at least one galactomannan or glucomannan is typically at most 95:5, such as at most 90:10, at most 85:15, at most 80:20, at most 75:25, at most 70:30, at most 65:35, at most 60:40, at most 55:45, at most 50:50, at most 45:55, at most 40:60, at most 35:65, at most 30:70, at most 25:75, at most 20:80, at most 15:85, at most 10:90, and at most 5:95. Depending on the gum, the weight ratio is preferably 60:40 (optimum for LBG), but 20/80 has been demonstrated to be excellent for xanthan/guar gum mixtures, and for yet other mixtures a 50/50 mixture has proven optimal, depending i.a. on the content of salts and the pH.

The compositions typically have a pH from between 1 to 8, depending on the field of use, where the lower end is e.g. useful for toilet cleaners etc, and the higher end values are useful in food and feedstuffs. Preferred pH values are about 1, about 1.5, about 2.0, about 2.5, about 3.0, about 3.5, about 4.0, about 4.5, about 5.0, about 5.5, about 6.0, about 6.5 and about 7.0.

An interesting group of compositions of the invention is constituted by food or feedstuff products. These will comprise a xanthan gum of the invention or a xanthan gum prepared according to the invention, or a composition discussed above, where also a glucomannan or galactomannan is included. A typical food or feedstuff of the invention is selected from the group consisting of a sauce, a dressing, a soup, a gravy, a jam, a fruit preparation, a frozen product, a bakery product, an ice cream, a beverage, a dairy product and an emulsion.

EXAMPLES

Methods Employed in Examples

LSV$_{max}$ and V$_{max}$ (0.3% Xanthan in 1% NaCl)

Xanthan gum solutions were prepared by dispersing the gum into deionised water and mixing for 15 minutes at 1000 rpm. Salts were then added and mixed for a further 5 minutes. LSV$_{max}$ viscosity was measured at a shear rate of 0.01 s$^{-1}$. V$_{max}$ viscosity was measured with a Brookfield LVT, spindle 2 at 1.5 rpm (Danisco Analytical Manual A2001). Gum concentrations and salt concentrations were varied according to the Figures.

LSV$_{vin}$ (0.3% Xanthan in 1% NaCl, pH 2.5)

Xanthan gum solutions were prepared by dispersing a gum/sugar blend into synthetic tap (0.14% NaCl+0.03% CaCl$_2$; 2H$_2$O) water and mixing for 5 minutes at 1000 rpm. NaCl and vinegar (12°) were then added and mixed for a further 10 minutes. Viscosity was measured at a shear rate of 0.01 s$^{-1}$.

LSV$_{salt}$ (0.3% Xanthan in 2.5% NaCl)

Xanthan gum solutions were prepared by dispersing the gum into salted water at 23±2° C. (2.5% NaCl) and mixing for 30 minutes at 500 rpm. Viscosity was measured at a shear rate of 0.01 s$^{-1}$.

Synergy Test (1% 60/40 Xanthan/LBG, 1% KCl)

1% KCl was dissolved in deionised water prior to the dispersion of 1% xanthan/LBG, 60/40. The dispersion was then placed in a water bath at 90° C. and mixed for 25 minutes. Evaporative losses were made good with hot deionised water before the hot solution was poured into the containers for gel strength measurement. The solution was then covered and cooled undisturbed and stored at room temperature overnight before gel strength measurements were made cf below. (Danisco Analytical Manual A1631)

Xanthan/LBG Xanthan/Tara Mixed Systems

The salt was dissolved in deionised water prior to the dispersion of xanthan/LBG or tara gum mixture. The dispersion was then placed in a water bath at 90° C. and heated with mixing until 85° C. The pH was adjusted if necessary with citric acid solution. Evaporative losses were made good with deionised water before the hot solution was poured into the containers for gel strength measurement. The solution was then cooled undisturbed and stored at room temperature overnight before measurements were made.

Xanthan/Guar Mixed Systems

The salt was dissolved in deionised water prior to the dispersion of the xanthan/guar mixture. The dispersion was then mixed at 800 rpm for 30 minutes. The pH was adjusted if necessary with citric acid. For the hot make-up the dispersion was placed in a water bath at 90° C. and heated with mixing until 85° C. Evaporative losses were made good with deionised water. The solution was then cooled to room temperature before measurements were made. Viscosity was measured using a Brookfield LVT, spindle 2 or 3 at 3 rpm.

Vinaigrette Model

Sugar (18 g), NaCl (2 g) and the xanthan/galactomannans were dispersed in synthetic tap water and placed in a water bath at 90° C. and mixed for 15 minutes. Evaporative losses were made good and the sample was cooled to room temperature before 36 g of vinegar was added. The final weight of solution was 200 g.

Rheological Measurements

Defined shear rate measurements of viscosity were made using an AR-1000 controlled stress rheometer. All viscoelastic measurements were made within the linear viscoelastic region of the material.

Automatic gap adjustment for temperature was used during the temperature ramp measurements.

Samples for gel strength were prepared in 80 mm diameter, 45 mm height containers and were measured after overnight storage at room temperature using a SMS TAXT+fitted with a ½ inch diameter flat ended probe programmed to penetrate the gel at 1 mm·s$^{-1}$. The gel strength was taken as the rupture point of the gel and expressed in Newtons (N)1N=101.9 g.

Acetate and Pyruvate Content

Puruvic acid and acetic acid was released from xanthan by hydrolysis and determined by High Performance Anion Exchange Chromatography (HPAEC). 3 g/l solutions of xanthan were prepared with deionised water and stirred overnight. Samples of 2 ml were hydrolysed by adding 4 ml of 1M HCl solution and storing for 6 hours in an oven at 100° C. without stirring. Cl$^-$ ions were then removed by filtration with Guard II Ag filters. Samples were analysed by HPAEC using a gradient elution method. A HPAEC Dionex system (Dionex Corporation) equipped with an anion-exchange column 4×250 mm (IonPac® AS11), a guard column 4×50 mm (IonPac®AG11) an eluent generator (EG50), with a 0.380 ml/min flow and suppressor (ASRS®-Ultra 4-mm) was used. Detection was made with a conductivity detector (DS3-1). (Danisco Analytical Manual A1991).

Example 1

20 Litre Scale Production of Improved Xanthan Gum

Xanthan gum was produced using various Xanthomonas strains at 20 l scale by fermentation of the microorganism in a nutrient medium containing at least one carbon source assimilable by the microorganisms and a source of nitrogen. The xanthan gum broth was subjected to a thermal treatment at 120° C. for 20 minutes before the xanthan gum was recovered from the broth by precipitation with alcohol. The precipitated xanthan was then dried to approximately 10% moisture and milled to produce a fine powder. The xanthan gum powder was tested with some simple viscosity tests. Table 3 below summarizes the initial screening results. Strain CFBP 176 was selected for further study due to the very high $V_{max}$ viscosity of the recovered xanthan gum which was approximately 40% higher than the average for the current standard commercial product Grindsted®Xanthan 80. This test correlates well with the low shear rate viscosity which is an indication of the potential suspension power of the gum. Higher values are known to correlate well with performance in many applications.

TABLE 3

Results of initial 20 l scale screening of CFBP 176.

| Strain | Broth reference XF 04 01 | Powder reference XE 04 01 | Acetic acid/ dry (%) | Pyruvic acid/ dry (%) | $V_{max}$ (mPa·s) |
|---|---|---|---|---|---|
| CFBP 176 | 168 C | 241-2 | 4.9 | 4.8 | 5600 |
| Xanthan 80* | | | 6.3 | 3.7 | 3464 |

*Average from 10 lots of commercial Grindsted Xanthan 80

The xanthan from strain CFBP 176 also had higher than average pyruvic acid content and lower than average acetic acid content. High pyruvate content is known to give higher viscosity xanthan gum, cf. above. It has also been suggested that reducing the acetate content is beneficial for the viscosity and synergy. The high $V_{max}$ viscosity of the CFBP 176 and acetate and pyruvate analyses results is consistent with this.

More detailed functionality testing of the xanthan produced by CFBP 176 was carried out and the results are summarised in Table 4.

TABLE 4

Functional testing of xanthan produced from CFBP 176.

| Reference | | LSV max (mPa·s) | LSV salt (mPa·s) | LSV vin (mPa·s) | V max (mPa·s) | Gel strength †(N) |
|---|---|---|---|---|---|---|
| Broth | Powder | | | | | |
| 04.01.168.C | XE.04.01.241-2 | 80 000 | 50 000 | 55 000 | 5200 | 11.0 |
| Grindsted ® Xanthan 80* | | 26 545 | 4455 | 10 500 | 3464 | 7.95 |

*Average from 10 lots of Xanthan 80
†1% 50/50 Xanthan/LBG, 1% KCl

The high viscosity at low shear rate was confirmed and also the gel strength with locust bean gum was found to be above average. All functional test results were significantly higher than the average of 10 current commercial production lots.

Example 2

Pilot Scale Optimisation of Process for CFBP 176

A series of 1000 l fermentation trials were conducted and the variables are summarised in Table 7. Xanthan gum was recovered from the broths under various conditions. The pH of the broth during heat treatment was varied between pH 5.5-11 in order to partially deacetylate the xanthan gum. The xanthan was recovered from the fermentation broth in the same manner as described in Example 1.

TABLE 5

Summary of the variables for the CFBP 176 fermentation trials.

| Broth Ref XF | Total Nitrogen (%) | Source Organic | Source Mineral | Nitrogen source Ratio Organic (%) | Nitrogen source Ratio Mineral (%) |
|---|---|---|---|---|---|
| 04.01.168.C | 0.055 | Soya | | 100 | 0 |
| 07.07.066.B | 0.078 | Soya | | 100 | 0 |
| 07.01.74 | 0.100 | Carob germ flour | NH$_4$NO$_3$ | 56 | 44 |
| 07.01.080.A | 0.086 | Soya | NH$_4$NO$_3$ + (NH$_4$)$_2$HPO$_4$ | 60 | 40 |
| 07.01.093.A | 0.086 | Soya | NH4NO3 | 60 | 40 |
| 07.01.093B | 0.078 | Soya | | 100 | 0 |
| 07.01.102.A | 0.050 | Soya | | 100 | 0 |
| 07.01.102.B | 0.070 | Soya | | 100 | 0 |
| 07.01.129.A | 0.081 | Soya | NH$_4$NO$_3$ | 60 | 40 |
| 07.01.146.A | 0.055 | Soya | | 100 | 0 |
| 07.01.146.B | 0.060 | Soya | NH$_4$NO$_3$ | 28 | 72 |
| 07.01.156.A | 0.055 | Soya | | 100 | 0 |
| 07.01.156.B | 0.055 | Soya | | 100 | 0 |
| 07.01.166.B | 0.055 | Soya | | 100 | 0 |
| 07.01.176.A | 0.062 | Soya | | 100 | 0 |

The functionality and the acetate and pyruvate content of the xanthan samples were tested. The average values for each of a number of parameters as a function of the pH of the thermal treatment at 120° C. have been calculated and are given in Tables 6 and 7:

TABLE 6

Average values from pilot scale preparations.

| pH | # of samples | LSV max (Pa·s) Mean | LSV max (Pa·s) SD | LSV salt (Pa·s) Mean | LSV salt (Pa·s) SD | LSV Vin (Pa·s) Mean | LSV Vin (Pa·s) SD | V max (mPa·s) Mean | V max (mPa·s) SD | Gel strength (N)† Mean | Gel strength (N)† SD | Acid sensitivity Mean | Acid sensitivity SD |
|---|---|---|---|---|---|---|---|---|---|---|---|---|---|
| 5.5 | 14 | 84.6 | 28.7 | 66.4 | 18.2 | 46.6 | 13.4 | 5345 | 1018 | 12.2 | 1.26 | 0.56 | 0.11 |
| 7.0 | 7 | 125.0 | 37.6 | 85.7 | 37.6 | 70.3 | 32.8 | 6386 | 999 | 13.1 | 1.26 | 0.53 | 0.19 |
| 8.0 | 3 | 85.0 | 33.0 | 53.7 | 38.2 | 37.3 | 23.7 | 4800 | 800 | 12.8 | 1.04 | 0.41 | 0.21 |
| 9.0 | 8 | 98.4 | 26.8 | 48.0 | 24.9 | 30.6 | 13.5 | 5388 | 843 | 13.0 | 1.24 | 0.31 | 0.15 |
| 9.5 | 6 | 105.8 | 31.3 | 39.7 | 24.5 | 32.8 | 22.0 | 5817 | 1478 | 12.9 | 1.19 | 0.28 | 0.14 |
| 10.0 | 4 | 111.8 | 34.0 | 24.5 | 23.9 | 27.5 | 19.8 | 5663 | 596 | 12.6 | 1.13 | 0.23 | 0.11 |
| 11.0 | 2 | 82.5 | 3.5 | 19.5 | 2.1 | 18.0 | 2.8 | 5250 | 71 | 13.2 | 0.28 | 0.22 | 0.04 |
| Av80* | 11 | 26.5 | 5.9 | 4.5 | 3.8 | 10.5 | 2.4 | 3464 | 353 | 7.95 | 0.99 | 0.43 | 0.16 |

*Average value for Grindsted ® Xanthan 80
†1% 50/50 Xanthan/LBG, 1% KCl

TABLE 7

Average values from pilot scale preparations

| pH | # of samples | Acetic Acid (%) Mean | Acetic Acid (%) SD | Pyruvic acid (%) Mean | Pyruvic acid (%) SD |
|---|---|---|---|---|---|
| 5.5 | 14 | 4.81 | 0.40 | 5.32 | 0.36 |
| 7.0 | 7 | 4.81 | 0.41 | 5.60 | 0.26 |
| 8.0 | 3 | 3.85 | 0.38 | 5.59 | 0.54 |
| 9.0 | 8 | 3.84 | 0.56 | 5.82 | 0.38 |
| 9.5 | 6 | 3.70 | 0.76 | 5.64 | 0.29 |
| 10.0 | 4 | 3.28 | 0.87 | 6.22 | 0.41 |

TABLE 7-continued

Average values from pilot scale preparations

| pH | # of samples | Acetic Acid (%) Mean | Acetic Acid (%) SD | Pyruvic acid (%) Mean | Pyruvic acid (%) SD |
|---|---|---|---|---|---|
| 11.0 | 2 | 1.06 | 0.57 | 6.41 | 0.18 |
| Av80* | 11 | 6.24 | 0.67 | 3.70 | 0.60 |

*Average value for Grindsted ® Xanthan 80

Table 6 shows that, regardless of the fermentation conditions and pH of the thermal treatment, xanthan produced from strain CFBP 176 had significantly better functionality in all the tests except acid sensitivity compared to a commercial product (Grindsted® Xanthan 80). Acid sensitivity was increased with increasing pH and was more sensitive than the commercial product when the pH of thermal treatment was pH 8.0 or above.

This is illustrated for samples prepared at pH 5.5 and 7 in FIG. 3. The data has been normalized relative to the results of the CFBP 176 treated at pH 5.5.

Although there is considerable variation for a given pH, the data nonetheless shows some interesting trends regarding the effect of the thermal treatment pH on the properties of xanthan gum produced from CFBP 176. For example, the low shear viscosity at neutral pH, ($LSV_{max}$), appears relatively unaffected by the pH of thermal treatment whereas the low shear viscosity at acidic pH 2.8, ($LSV_{vinaigrette}$)/decreases as the pH of the thermal treatment increases above pH 7 (FIG. 4a). This can be expressed as sensitivity to pH by calculation of the ratio between the two viscosities:

$$\frac{LSV \text{ vinaigrette}}{LSV \text{ max}}$$

The closer this value is to 1, the less sensitive the low shear viscosity of the xanthan is to low pH (FIG. 4b). Xanthan with a high ratio is believed to be of benefit in low pH applications such as food dressings and beverages.

As would be expected the acetic acid content of the xanthan gum is reduced as the pH is increased (FIG. 5). Interestingly there appears to be a slight increase in the pyruvic acid content as the pH increases.

FIG. 6 reveals that the low pH viscosity and hence pH sensitivity is closely linked to the acetic acid content. The sensitivity appears to reach a plateau at about 3% acetic acid at which point the low pH viscosity is approximately 20% of the neutral pH viscosity. A virtually identical relationship is seen for acetic acid content and $LSV_{salt}$ (FIG. 7), which is a measure of the ability of the xanthan gum to hydrate directly into a salt solution.

It has been widely reported that synergy of xanthan gum with galactomannans is dependent on the acetate content of the xanthan gum. However the results with xanthan from CFBP 176 do not show this trend as there is no significant change in the gel strength with LBG with decreasing acetic acid content (FIG. 8). However what is evident is that the xanthan from CFBP 176 has significantly higher gel strength with LBG than the standard commercial product Grindsted® Xanthan 80 regardless of the pH of the thermal treatment.

Conclusions from Pilot Scale Experiments

Using average values from all data at 120° C., it was found that increasing the pH of thermal treatment 1) has no effect on $LSV_{max}$ and $V_{max}$ viscosity, 2) increases the pH sensitivity of the xanthan gum, 3) decreases acetic acid content, 4) increases pyruvic acid content, 5) has no effect of gel strength with LBG, 6) increases $LSV_{salt}$ from pH 5.5 to pH 7.0 but then decreases at higher pH values, and 7) increases $LSV_{vin}$ from pH 5.5 to pH 7.0 but then decreases at higher pH values. So, in brief, increasing the pH of the broth from 5.5 to 7.0 has a beneficial effect on the functionality of the xanthan gum, whereas further increases have an overall negative effect on functionality. Based on the process optimization results, the optimum pH for thermal treatment was found to be pH 7. At this pH the gel strength and the low shear viscosity in acid were both high. Further increases in the pH had no significant effect on gel strength but the low shear viscosity in acid decreased.

Example 3

Industrial Production with Strain CFBP 176

Three industrial scale production trials were made using strain CFBP 176 by fermentation of the microorganism in a nutrient medium containing at least one carbon source assimilable by the microorganisms and a source of nitrogen. The results of the fermentation were in line with those expected from standard production. The xanthan from the 3 operations were precipitated with alcohol after the heat treatment described in Table 8 and the QC test results on the finished product are given in Table 9.

TABLE 8

Heat treatment conditions for the industrial scale fermentation trials of CFBP 176.

| Trial | | 1 | 2 | 3 |
|---|---|---|---|---|
| Heat treatment | Temperature | 110° C. | 120° C. | 120° C. |
| Heat treatment | pH | 7.0 | 7.0 | 7.5 |

TABLE 9

Quality control test results for finished product recovered from the industrial scale fermentation trials with CFBP 176.

| | | Trial | | |
|---|---|---|---|---|
| Test | Specification | 1 | 2 | 3 |
| Appearance | Pass/fail | Pass | Pass | Pass |
| Colour evaluation | Pass/fail | Pass | Pass | Pass |

TABLE 9-continued

Quality control test results for finished product recovered from the industrial scale fermentation trials with CFBP 176.

| | | Trial | | |
|---|---|---|---|---|
| Test | Specification | 1 | 2 | 3 |
| Whiteness | <100 | 75 | 74 | 76 |
| Colour a* | | 1.6 | 1.6 | 1.4 |
| Colour b* | | 18.6 | 19.2 | 18.0 |
| Colour L* | | 83 | 83 | 84 |
| Foreign particles per g | 0 à 30 | 15 | 10 | 1 |
| Screen <180 μm (FRG) | >95.0% | 99.4 | 99.4 | 99.2 |
| Screen <250 μm (FRG) | >99.5% | 99.9 | 99.9 | 99.9 |
| Loss on drying | 6.0 à 12.0% | 6.3 | 6.5 | 9.4 |
| Viscosity KCl | 1300 à 1700 mPa · s | 1400 | 1400 | 1380 |
| pH | | 7.0 | 7.2 | 7.2 |
| Isopropanol | <500 mg/kg | | | 24 |
| Vmax | >4800 mPa · s | 7100 | 6320 | 6360 |

All 3 industrial production lots were within the specifications for standard xanthan gum and all 3 lots gave a high V max viscosity which was close to that seen in the pilot scale trials at 120° C., pH 7 and significantly higher than the average of 10 current commercial production lots (3464 mPa·s).

The acetate and pyruvate contents of the samples are given in Table 10 and show that the xanthan from CFBP 176 has a high pyruvate content compared to the average for a standard commercial product. This is in line with the results seen in the pilot scale trials, cf. above. The acetate content is similar to the standard product and higher than seen with the pilot scale samples.

TABLE 10

Acetate and pyruvate content of xanthan from CFBP 176.

| Sample | Thermal treatment (° C.) | pH at thermal treatment | Acetic acid (%) | Pyruvic acid (%) |
|---|---|---|---|---|
| CFBP 176 (trial 1) | 110 | 7.0 | 6.35 | 6.00 |
| CFBP 176 (trial 2) | 120 | 7.0 | 6.46 | 7.11 |
| CFBP 176 (trial 3) | 120 | 7.5 | 5.10 | 6.49 |
| CFBP 176 pilot scale average | 120 | 7.0 | 4.80 | 5.60 |
| Grindsted ® Xanthan 80 (average) | 120 | 5.5 | 6.20 | 3.70 |

Example 4

Functional Characterisation of Xanthan Produced from CFBP 176

The functional characteristics of the 3 industrial production lots have been studied and compared to a current standard commercial product Grindsted® Xanthan 80 (Danisco). Synergistic interactions with galactomannans and glucomannans have been studied. Meyprodor™ 400 lot 14859 (Danisco) was used as the guar reference and Meypro Fleur® M-175 lot 4760597461 (Danisco) was used as the locust bean gum reference. In addition the solution rheology has been characterized. Table 11 summarizes the basic characteristics of the commercial sample used in the comparison, the average values from the pilot scale production samples and the 3 industrial lots of CFBP 176.

TABLE 11

The basic functional characteristics of Grindsted ® Xanthan 80, pilot and industrial scale CFBP 176.

| Test | Grindsted ® Xanthan 80 | CFBP 176 pilot scale average (120° C., pH 7) | CFBP 176 (trial 1) | CFBP 176 (trial 2) | CFBP 176 (trial 3) |
|---|---|---|---|---|---|
| $LSV_{max}$ (mPa·s) | 32 000 | 125 000 | 125 000 | 95 000 | 86 000 |
| $LSV_{vin}$ (mPa·s) | 15 000 | 70 300 | 40 000 | 52 000 | 48 000 |
| $LSV_{Salt}$ (mPa·s) | 1 500 | 85 700 | 9 000 | 16 000 | 7 000 |
| $V_{max}$ (mPa·s) | 3 500 | 6 386 | 6 800 | 6 700 | 6 200 |
| Synergy test (N) | 10.4 | — | 17.1 | 17.5 | 18.1 |
| Gel strength† (N) | 7.5 | 13.1 | 14.0 | 16.0 | 14.0 |
| pH sensitivity ($LSV_{vin}/LSV_{max}$) | 0.46 | 0.53 | 0.32 | 0.55 | 0.56 |
| Acetate (%) | 6.19 | 4.80 | 6.35 | 6.46 | 5.10 |
| Pyruvate (%) | 3.85 | 5.60 | 6.00 | 7.11 | 6.49 |

†1% 50/50 Xanthan/LBG, 1% KCl

The xanthan from CFBP 176 produced at industrial scale had much better overall functionality compared to the standard product and, in general, gave similar functionality to the samples produced at pilot scale (FIG. 9). The exception was the $LSV_{salt}$ viscosity. Although the $LSV_{salt}$ viscosity of CFBP 176 was still better than the Grindsted® Xanthan 80, it was well below the potential seen at pilot scale and further work is needed to establish which process parameters influence this functionality at an industrial scale fermentation.

Example 5

Synergy with Locust Bean Gum

The high synergy seen in the pilot and lab scale productions was seen to an even greater extent with the 3 industrially produced lots. The gel strength as a function of xanthan/LBG ratio at neutral and acidic pH is shown in FIG. 10, which demonstrates that compared to a standard commercial product, the xanthan produced from strain CFBP 176 has significantly higher gel strength at all ratios tested. In addition, there is no change in gel strength between pH 7 and pH 3.5. In contrast, the gel strength of the standard commercial xanthan is reduced at pH 3.5. It is generally accepted that the synergistic interactions between xanthan and galactomannans are reduced as the pH becomes more acidic. This makes the result with the xanthan from CFBP 176 surprising.

The results underlying the depiction in FIG. 10 are provided in the following table:

| | | Gel strength (N) | | % |
|---|---|---|---|---|
| Xanthan | LBG | CFBP 176 | Xanthan 80 | increase |
| 1% gum, 0.5% NaCl pH as is | | | | |
| 20 | 80 | 3 | 1.7 | 76.5 |
| 30 | 70 | 6.5 | 3.4 | 91.2 |
| 40 | 60 | 10 | 5.3 | 88.7 |
| 50 | 50 | 12 | 7.3 | 64.4 |
| 60 | 40 | 14 | 7.8 | 79.5 |
| 70 | 30 | 14 | 7.6 | 84.2 |
| 80 | 20 | 9.6 | 4.7 | 104.3 |
| 1% gum, 0.5% NaCl pH 3.5 | | | | |
| 20 | 80 | 2.5 | 1 | 150.0 |
| 30 | 70 | 6.5 | 2 | 225.0 |
| 40 | 60 | 8 | 3 | 166.7 |
| 50 | 50 | 12 | 5 | 140.0 |
| 60 | 40 | 14.5 | 5 | 190.0 |
| 70 | 30 | 12.5 | 5 | 150.0 |
| 80 | 20 | 12 | 4 | 200.0 |
| 90 | 10 | 6 | 1 | 500.0 |

A more detailed examination of the effect of pH on the gel strength at a fixed xanthan/LBG ratio of 60/40 shows that the gel strength with CFBP 176 is constant between pH 7 and approximately pH 3.5 whereas the commercial product is constant only down to pH 4.5 (FIG. 11). It can also be seen that the gel strength is higher for the CFBP 176 xanthan gum at any given pH. These differences were seen with all 3 lots produced at industrial scale. This improved performance at low pH is believed to be significant for applications such as culinary and beverage products where mixed xanthan gum/galactomannan systems are typically used in the pH range of pH 3 to pH 4.

The data underlying the depiction in FIG. 11 is shown in the following table

| 1% gum, 60/40 Xanthan/LBG, 0.5% NaCl. | | | |
|---|---|---|---|
| | Gel strength (N) | | % |
| pH | CFBP 176 | Xanthan 80 | increase |
| 4.6 | 14.4 | 6.6 | 118.2 |
| 3.5 | 14.5 | 5 | 190.0 |
| 2.8 | 3.7 | 2.9 | 27.6 |
| 2.5 | 1.5 | 0.36 | 316.7 |

Compared to Grindsted® Xanthan 80, the xanthan produced from CFBP 176 also exhibits higher synergy with LBG in the presence of salts (FIGS. 12a and 12b). This could be of benefit in salty foods such as meat, fish, dressings, sauces and soups. The data underlying FIGS. 12a and 12b are shown in the following table:

| 1% gum, 60/40 xanthan/LBG | | | |
|---|---|---|---|
| | Gel strength (N) | | |
| | CFBP 176 | Xanthan 80 | % increase |
| KCl | | | |
| 0.1 | 10 | 4 | 150.0 |
| 0.5 | 14 | 8 | 75.0 |
| 0.75 | 18 | 10 | 80.0 |
| 1 | 18 | 9 | 100.0 |
| 2 | 18 | 9 | 100.0 |
| 3 | 17 | 10 | 70.0 |
| 4 | 17 | 10 | 70.0 |
| NaCl | | | |
| 0.1 | 6 | 3.3 | 81.8 |
| 0.5 | 14 | 8 | 75.0 |
| 0.75 | 13 | 7 | 85.7 |
| 1 | 14 | 6 | 133.3 |
| 1.5 | 10 | 6.5 | 53.8 |
| 2 | 9 | 5 | 80.0 |
| 3 | 9 | 5 | 80.0 |
| 4 | 8 | 4.5 | 77.8 |

Table 12 and FIG. 13 shows that, in a model vinaigrette, the xanthan from CFBP 176 when mixed with LBG, (60:40 xanthan:LBG), provides a higher elastic modulus compared to the equivalent with a standard xanthan gum. For example, 0.2% of the mixture with a standard xanthan was required to achieve the same elastic modulus obtained with only 0.15% of xanthan from CFBP 176. The difference was even more marked at lower concentrations. For example the mixture containing the xanthan from CFBP 176 gave approximately 50% higher elastic modulus at 0.05% compared to a standard xanthan. High elastic modulus is well known to correlate with better suspension power and would be of benefit for suspension of emulsions and particles in a wide range of food applications.

TABLE 12

Effect of gum concentration on the elastic modulus, G' of a 60:40 mixture of xanthan:LBG in a vinaigrette formulation (1% NaCl, pH 2.5).

| | Elastic modulus, G' at 1 rad · s$^{-1}$ (Pa) | | |
|---|---|---|---|
| Concentration (%) | CFBP 176 (trial 1) | Grindsted ® Xanthan 80 | % increase |
| 0.2 | 2.53 | 1.78 | 42.1 |
| 0.15 | 1.73 | 0.22 | 686.4 |
| 0.1 | 0.45 | 0.16 | 181.3 |
| 0.05 | 0.11 | 0.06 | 83.3 |

Example 6

Synergy with Guar Gum

The xanthan from CFBP 176 gave higher viscosity and elastic modulus in mixtures with guar gum compared to a standard xanthan gum and this difference was increased when the samples were prepared with a hot make-up process in which the solution was placed in a water bath at 90° C. for 15 minutes (FIGS. 14 and 15). The xanthan from CFBP 176 gave higher viscosity and elastic modulus over a very broad pH range compared to a standard xanthan gum (FIG. 16). This improved performance at low pH could be significant for applications such as culinary and beverage where mixed xanthan gum/galactomannan systems are typically used in the pH range of pH 3 to pH 4.

Table 13 shows that, in a model vinaigrette, the xanthan from CFBP 176 when mixed with guar gum, (20:80 xanthan:guar), gives a higher elastic modulus and Brookfield viscosity compared to the equivalent with a standard xanthan gum. For example, approximately 0.3% of the mixture with a standard xanthan was required to achieve a similar elastic modulus and viscosity to that obtained with only 0.20% of xanthan from CFBP 176. High elastic modulus is well known to correlate with better suspension power and would be of benefit for suspension of emulsions and particles in a wide range of food applications.

TABLE 13

Effect of gum concentration on the elastic modulus, G' and viscosity of a 20:80 mixture of xanthan:guar in a vinaigrette formulation (1% NaCl, pH 2.5).

| | Elastic modulus at 1 rad · s$^{-1}$ (Pa) | | Brookfield viscosity 3 rpm (mPa · s) | |
|---|---|---|---|---|
| Concentration (%) | Grindsted ® Xanthan 80 | CFBP 176 trial 1 | Grindsted ® Xanthan 80 | CFBP 176 trial 1 |
| 0.1 | 0.0001 | 0.0065 | 4 | 24 |
| 0.2 | 0.012 | 0.06 | 44 | 140 |
| 0.3 | 0.087 | 0.22 | 238 | 500 |
| 0.4 | 0.29 | 0.33 | 670 | 700 |
| 0.5 | 0.91 | 1.22 | 2260 | 3080 |

Example 7

Synergy with Other Galactomannans and Glucomannans

Xanthan from CFBP 176 also shows higher synergy with the galactomannan Tara gum lot ex 012684 (Exandal). It gave optimum gel strength at higher xanthan gum content than the standard xanthan and was similar to the optimum with xanthan/LBG (FIG. 17a). The gel strength was close to that obtained with a standard xanthan gum with LBG. This suggests that the tara gum, when used with the xanthan from CFBP 176 could be an alternative to LBG. The xanthan from CFBP 176 only showed higher synergy with konjac glucomannan (Konjac powder prod N° 455312, lot 7110806192, Danisco) at gum ratios above 60% xanthan gum. Below 60% xanthan gum content the gel strength was very similar to the mixture with a standard xanthan gum (FIG. 17b).

Example 8

Solution Rheology

The 3 industrial lots from Example 4 gave very similar flow profiles in both 1% NaCl and in 1% NaCl, pH 2.5 as shown in FIGS. 18a and 18b.

Xanthan produced from strain CFBP 176 had significantly higher low shear viscosity than a standard commercial xanthan gum in 1% NaCl and in 1% NaCl at pH 2.5 (FIGS. 19a and 19b). This is also supported by the viscoelastic profile shown in FIG. 20 which shows a more elastic-like profile in 1% NaCl. This is indicated by the higher elastic modulus (G'), the lower dependence on frequency and the presence of a cross-over between the elastic modulus (G') and the viscous modulus (G") in the CFBP 176. These results are consistent with the high pyruvate content of the CFBP 176 compared to the standard commercial xanthan. The greater elasticity in the solution indicates stronger interactions between the xanthan gum molecules and results in the high viscosity at low shear and provides more suspension power. The greater suspension power may allow for a reduction in the use level with the CFBP 176 whilst still maintaining an equivalent product stability and texture to that achieved with Grindsted® Xanthan 80. FIGS. 21 and 22 show that the xanthan from CFBP 176 can give a low shear viscosity (<0.01 s$^1$) equivalent to that of Grindsted®Xanthan 80 at between 25 and 40% lower concentration depending on the system. However the CFBP 176 solutions are slightly more pseudoplastic and so the viscosity at higher shear rates is lower. This may have some impact on the overall texture of the product. A similar trend is seen with the elastic modulus which consistently provides equivalent elastic modulus values at approximately 30% lower concentration compared to the Grindsted®Xanthan 80 in the concentration range of 0.05-0.5% (FIG. 23).

Solutions of xanthan gum undergo a conformational transition during heating which is believed to be associated with the change from a rigid ordered state at low temperature to a more flexible, disordered state at high temperatures. This conformational change was first observed as a sigmoidal change in viscosity. The conformational transition of 0.5% solutions of xanthan from CFBP 176 has been measured at 10 s$^{-1}$ as a function of temperature at different NaCl concentrations and compared to Grindsted® Xanthan 80. An example of the results is shown in FIG. 24.

An interesting feature can be seen in FIG. 24. Prior to the onset of the conformational transition, the viscosity of CFBP 176 is virtually constant whereas the viscosity of the commercial product decreases with increasing temperature.

Example 9

Summary of Functional Testing Results

In order to illustrate the high performance of the xanthan gum from CFBP 176 in comparison with Grindsted® Xanthan 80, spider graphs have been drawn from various results taken from the functional characterisation (FIGS. 25 and 26). In each case the data has been normalised to the value of the CFBP 176 and the Grindsted® Xanthan 80 has been plotted relative to this. The keys to FIGS. 26 and 27 are given in Tables 14 and 15 respectively and they give a brief description of the measurements and the origin of the data.

TABLE 14

Key to FIG. 25.

| KEY | Description of measurement | Source |
|---|---|---|
| LBG | Gel strength of 1% gum, 60/40 xanthan/LBG in 0.5% NaCl | FIG. 10 |
| LBG low pH | Gel strength of 1% gum, 60/40 xanthan/LBG in 0.5% NaCl, pH 3.0 | FIG. 11 |
| LBG salt | Gel strength of 1% gum, 60/40 xanthan/LBG in 2% NaCl | FIG. 12a |
| Guar | Viscosity of 0.3% gum, 80/20 guar/xanthan in 1% NaCl (Hot make-up) | FIG. 14b |
| Guar low pH | Viscosity of 0.3% gum, 50/50 guar/xanthan in 9% sucrose + 1% NaCl at pH 3.0 | FIG. 14a |
| Tara | Gel strength of 1% gum, 50/50 xanthan/tara in 0.5% NaCl | FIG. 17a |

TABLE 15

Key to FIG. 26.

| KEY | Description of measurement | Source |
|---|---|---|
| V$_{max}$ | Viscosity of 0.3% xanthan in 1% NaCl (Brookfield, 1.5 rpm) | Table 11 |
| Neutral pH suspension power (LSV$_{max}$) | Viscosity at 0.01 s-1 of 0.3% xanthan in 1% NaCl. | Table 11 |
| Salt hydration | Viscosity at 0.01 s-1 of 0.3% xanthan after 30 mins hydration in 2.5% NaCl (500 rpm) | Table 11 |
| Low pH suspension power (LSV$_{vin}$) | Viscosity at 0.01 s-1 of 0.3% xanthan in 1% NaCl, pH 2.5 | Table 11 |
| pH sensitivity | Ratio of LSV vin/LSV max | Table 11 |
| Temperature stability | Ratio of viscosity at 60° C./ viscosity at 20° C. | FIG. 24 |

The invention claimed is:

1. A composition comprising a xanthan gum in admixture with at least one galactomannan or glucomannan, wherein the xanthan gum has the following characteristics:
   a pyruvic acid content of at least 5.0% (w/w),
   a pyruvic acid to acetic acid w/w ratio of at least 0.5,
   a low shear viscosity (LSV$_{max}$) measured at 0.3% xanthan in 1% NaCl at a shear rate of 0.01 s$^{-1}$ at 23 ±2° C. of at least 80 Pa·s, and a gel strength with locust bean gum (LBG) measured at 1% gum (60:40 Xanthan/LBG) in 1% KCl of at least 13.0 N, and wherein the xanthum gum is a product of a *Xanthomonas* strain selected from the group consisting of strains CFBP 19, CFBP 176, CFBP 64, CFBP 412, ATCC 17915, ATCC 19046, and CFBP 1847, or which is a product of a derivative or progeny of any one of strains CFBP 19, CFBP 176, CFBP 64, CFBP 412, ATCC 17915, ATCC 19046, and CFBP 1847.

2. The composition according to claim 1, wherein the at least one galactomannan is selected from the group consisting of guar gum, tara gum, locust bean gum, cassia gum, and wherein the glucomannan is konjac glucomannan.

3. The composition according to claim 1, which further comprises a salt.

4. The composition according to claim 1, wherein the weight ratio between the xanthan gum and the at least one galactomannan or glucomannan is at least 5:95, at least 10:90, at least 15:85, at least 20:80, at least 25:75, at least 30:70, at least 35:65, at least 40:60, at least 45:55, at least 50:50, at least 55: 45, at least 60:40, at least 65:35, at least 70:30, at least 75:25, at least 80:20, at least 85:15, at least 90:10, or at least 95:5.

5. The composition according to claim 4, wherein the weight ratio between the xanthan gum and the at least one galactomannan or glucomannan is at most 95:5, at most 90:10, at most 85:15, at most 80:20, at most 75:25, at most 70:30, at most 65:35, at most 60:40, at most 55:45, at most 50:50, at most 45:55, at most 40:60, at most 35:65, at most 30:70, at most 25:75, at most 20:80, at most 15:85, at most 10:90, or at most 5:95.

6. The composition according to claim 4, where the ratio is about 60:40.

7. A food or feedstuff product comprising a composition according to claim 1.

8. The food or feedstuff according to claim 7 selected from the group consisting of a sauce, a dressing, a soup, a gravy, a jam, a fruit preparation, a frozen product, a bakery product, an ice cream, a beverage, and an emulsion.

9. The composition according to claim 1, wherein the composition exhibits a high temperature stability as expressed as a ratio between viscosities at 60° C. and 20° C.

10. The composition according to claim 9, wherein the ratio is at least 0.75.

11. The composition according to claim 9, wherein the ratio is at least 0.85.

12. The composition according to claim 9, wherein the ratio is at least 0.9 to 1.0.

\* \* \* \* \*